US012571737B2

(12) United States Patent
Guizani et al.

(10) Patent No.: US 12,571,737 B2
(45) Date of Patent: Mar. 10, 2026

(54) QUANTITATIVE RAMAN SPECTROSCOPY

(71) Applicant: AALTO UNIVERSITY FOUNDATION SR, Aalto (FI)

(72) Inventors: Chamseddine Guizani, Aalto (FI); Sanna Hellsten, Aalto (FI); Joanna Witos, Aalto (FI)

(73) Assignee: AALTO UNIVERSITY FOUNDATION SR, Aalto (FI)

( * ) Notice: Subject to any disclaimer, the term of this patent is extended or adjusted under 35 U.S.C. 154(b) by 0 days.

(21) Appl. No.: 17/623,460

(22) PCT Filed: Jun. 26, 2020

(86) PCT No.: PCT/EP2020/068087
§ 371 (c)(1),
(2) Date: Dec. 28, 2021

(87) PCT Pub. No.: WO2020/260625
PCT Pub. Date: Dec. 30, 2020

(65) Prior Publication Data

US 2022/0364997 A1 Nov. 17, 2022

(30) Foreign Application Priority Data

Jun. 28, 2019 (FI) ..................................... 20195573

(51) Int. Cl.
*G01N 21/65* (2006.01)
*G01N 21/94* (2006.01)
(Continued)

(52) U.S. Cl.
CPC ............. *G01N 21/65* (2013.01); *G01N 21/94* (2013.01); *G01N 33/182* (2013.01); *G01J 3/44* (2013.01)

(58) Field of Classification Search
CPC ...... G01N 21/65; G01N 21/94; G01N 33/182; G01J 3/44
See application file for complete search history.

(56) References Cited

U.S. PATENT DOCUMENTS 5,404,218 A * 4/1995 Nave ..................... G01N 21/65 356/246
2003/0130823 A1* 7/2003 Potyrailo .................. G01J 3/28 702/189
(Continued)

FOREIGN PATENT DOCUMENTS

WO WO-2006086873 A1 * 8/2006 ............. G01N 21/65
WO WO-2018191445 A1 * 10/2018 ............. B01J 4/008

OTHER PUBLICATIONS

Hauru, L.K., Hummel, M., Nieminen, K., Michud, A. and Sixta, H., 2016. Cellulose regeneration and spinnability from ionic liquids. Soft matter, 12(5), pp. 1487-1495. (Year: 2016).*
(Continued)

*Primary Examiner* — Uzma Alam
*Assistant Examiner* — Mohamed Doumbia
(74) *Attorney, Agent, or Firm* — Buchanan Ingersoll & Rooney PC

(57) ABSTRACT

Disclosed is a method for quantification of water and/or one or more ionic liquid components in an ionic liquid (IL)/ water (H2O) mixture. The method comprises obtaining one
(Continued)

or more Raman spectra for the IL/H2O mixture, and using a quantitative calibration model with the one or more Raman spectra to quantify water and/or one or more ionic liquid components in the IL/H2O mixture.

17 Claims, 26 Drawing Sheets

(51) Int. Cl.
*G01N 33/18* (2006.01)
*G01J 3/44* (2006.01)

(56) References Cited

U.S. PATENT DOCUMENTS

| | | | | |
|---|---|---|---|---|
| 2011/0200776 | A1* | 8/2011 | Zikeli | C08L 1/02 428/36.9 |
| 2011/0222055 | A1* | 9/2011 | Durickovic | G01N 21/65 356/301 |
| 2016/0053407 | A1* | 2/2016 | Michud | D01F 2/02 536/56 |
| 2017/0319060 | A1* | 11/2017 | Huang | A61B 3/102 |
| 2020/0002848 | A1* | 1/2020 | Sixta | B29C 48/022 |
| 2020/0400836 | A1* | 12/2020 | Nguyen | G01S 17/95 |

OTHER PUBLICATIONS

Hauru, 2016. Cellulose regeneration and spinnability from ionic liquids. Soft matter, 12(5), pp. 1487-1495 (Year: 2016).*

International Search Report (PCT/ISA/210) and Written Opinion (PCT/ISA/237) mailed on Sep. 16, 2020, by the European Patent Office as the International Searching Authority for International Application No. PCT/EP2020/068087.

Hauru, Lauri K.J. et al., "Dry jet-wet spinning of strong cellulose filaments from ionic liquid solution", Cellulose, Sep. 14, 2014, vol. 21, No. 6, pp. 4471-4481.

Michud, Anne et al., "Ionecell-F: ionic liquid-based cellulosic textile fibers as an alternative to viscose and Lyocell", Textile Research Journal, Jun. 16, 2015, vol. 86, No. 5, pp. 543-552.

Guizani, Chamseddine et al., "Quantitave Raman spectroscopy for the Ioncell™ process. Part 1: comparison of univariate and multivariate calibration methods for the quantification of water and protic ionic liquid components", Cellulose, Nov. 2, 2019, vol. 27, No. 1, pp. 157-170.

* cited by examiner (1) (2) (3)

QUANTITATIVE RAMAN SPECTROSCOPY

FIELD

The present invention relates to quantitative Raman Spectroscopy. In particular, the disclosure may relate to Quantitative Raman Spectroscopy for the Ioncell-F process.

BACKGROUND

Ex-situ analytical techniques such as High Performance Liquid Chromatography (HPLC), Ion Chromatography (IC), Capillary Electrophoresis (CE) can be used to determine the anion or cation concentrations, while Nuclear Magnetic Resonance (NMR) spectroscopy can be used to determine the acid-to-base (A:B) ratio. $H_2O$ concentration in ionic liquid (IL)/water ($H_2O$) mixtures can be determined by Karl Fisher (KF) titration [3] [5].

The determination of $H_2O$ concentration in IL/$H_2O$ mixtures utilizing Refractive Index (RI) measurement is a simple and robust method for on-line analysis in a continuous process. However, this method is not sensitive to A:B ratio variation in IL/$H_2O$ mixtures (results not shown). On top of that, many of the methods cited above are time consuming and tedious, and not suitable for process on-line analysis.

SUMMARY

Ioncell-F is a new process for the production of Lyocell-type man-made cellulosic fibers based on cellulose pulp dissolution in an ionic liquid (IL), dry-jet wet spinning of the solution (spinning dope) in a water ($H_2O$) bath and a subsequent solvent recovery step, in which the IL and $H_2O$ are separated. The whole process is operated in a closed-loop system [1].

The Ioncell-F process runs on non-imidazolium based protic ILs, among which for example [DBNH] [OAc] and [mTBDH] [OAc] have shown high potential for the production of strong cellulose fibers with minimal cellulose degradation [1] [2] [3].

The acid-to-base molar ratio in the IL (A:B ratio) and the $H_2O$ content in IL/$H_2O$ mixtures are critical parameters for the cellulose dissolution and cellulose dope spinning. Water as a non-solvent can hinder the cellulose dissolution if its concentration in the IL/$H_2O$ mixtures reaches a certain limit (usually few percent). Acetic acid acts also as a non-solvent if it is in excess compared to the base and prevent a good cellulose dissolution. In addition, the presence of water in the cellulose dope can affect the spinning by modifying the rheological properties of the dope (water acts as a softener). The A:B ratio and $H_2O$ contents can vary substantially inside the process loop. For instance, $H_2O$ concentration will decrease gradually between the spinning bath and the solvent recovery/purification steps. Also, the A:B ratio may change because of different acid and base vapor pressures or due to reactive azeotrope formation during recovery/purification steps using for instance evaporation and distillation [2] [4] [5]. To ensure a good process stability and a homogenous fibers quality, those parameters should be well adjusted in each unit operation. Therefore, their fast and quantitative monitoring is an important part of the process control.

The development of fast, quantitative online analytical methods for the simultaneous determination of $H_2O$ concentration and A:B ratio in IL/$H_2O$ mixtures can benefit an increasing number of emerging processes based on IL/$H_2O$ mixtures, for example, in biomass fractionation, pulp upgrading, or protein separation [6]-[9].

Vibrational spectroscopy methods have the big advantages of being fast, non-destructive, and requiring much less efforts and time for sample preparation. In addition to the classical KF titration method as well as to various electrochemical methods [10] [11], vibrational spectroscopy excels in detecting and analyzing water contained in ILs. For instance, Viell at al. [12] developed a quantitative method for the determination of the composition of binary mixtures of water and various ILs using mid-infrared (mid-IR) spectroscopy. Also, Near-infrared (NIR) spectroscopy was successfully used for the non-invasive and in situ determination of concentrations and the structure of water absorbed by room-temperature ILs [13].

Raman spectroscopy is a well-known vibrational spectroscopy technique, based on the inelastic scattering of the light by a material. The proportional relationship between Raman scattering intensity and analyte concentration is the basis for most of the quantitative analysis done using Raman spectroscopy in gaseous, liquid, or solid samples [14]. In addition, Raman spectroscopy is also well suited for quantitative analysis of multiple components in a sample because a single Raman spectrum often contains enough information to determine their concentration simultaneously [15]. The use of Raman probes and optical fibers also allows remote monitoring of processes in hostile environments, which makes the technique very suitable for on-line analysis.

Raman spectroscopy has been widely used for the investigation of the intermolecular interactions, structures, and band assignment in pure ILs and mixtures of ILs [16] [17] [18]. Nevertheless, methods for quantitative measurements of concentrations in IL/$H_2O$ mixtures are scarcely investigated in the literature.

In this application, we discuss the potential of Raman spectroscopy combined with univariate and multivariate calibrations for the fast and quantitative determination of $H_2O$, Acid, and Base contents in a wide and process-relevant range of $H_2O$/IL mixtures.

In particular, we investigate in this application the potential of Raman spectroscopy for the quantification of protic ionic liquid components (acid and base) and water, in ionic liquid/water mixtures, taking 1.5-Diazabicyclo[4.3.0]non-5-ene/Acetate ([DBNH] [OAc]) as a case study. We show that the combination of Raman spectroscopy and Chemometrics is successful for the quantitative analysis of the ionic liquid components and water in mixtures over wide concentration ranges. The finding of the present work suggest that Raman spectroscopy should be considered more universally for the in-line monitoring and control of processes involving Ionic Liquid/$H_2O$ mixtures.

In this application we have shown that Raman spectroscopy in combination with univariate or multivariate calibration can be applied successfully for the quantitative analysis of protic IL components and H2O in IL/$H_2O$ mixtures. Compared to the univariate calibration, the multivariate calibration using PLS regression showed excellent performance for the quantitative analysis of the IL components and water over wide concentration ranges. These results suggest that the combination of Raman spectroscopy and Chemometrics could be applied more universally to monitor and control a variety of processes involving the use of IL/$H_2O$ mixtures.

The disclosure includes comparison of univariate and multivariate calibration methods for the quantification of water and protic ionic liquid components. The disclosure includes keywords: Ioncell-F, Ionic liquid, Raman spectroscopy, Chemometrics.

According to a first aspect, a method for quantification of water and/or one or more ionic liquid components in an ionic liquid (IL)/water ($H_2O$) mixture is disclosed. The method comprises obtaining one or more Raman spectra for the IL/$H_2O$ mixture and using a quantitative calibration model with the one or more Raman spectra to quantify water and/or one or more ionic liquid components in the IL/$H_2O$ mixture.

In an embodiment, the ionic liquid is a protic ionic liquid.

In an embodiment, the ionic liquid is or comprises a non-imidazolium based protic ionic liquid.

In an embodiment, using a quantitative calibration model involves univariate calibration, which is based on finding a relationship between single spectral variable, such as peak intensity, peak area and/or peak shift, and an analyte concentration.

In an embodiment, the method comprises determining $H_2O$ concentration in the IL/$H_2O$ mixture utilizing a linear relationship between $H_2O$ peak area and the $H_2O$ mass fraction in the IL/$H_2O$ mixture.

In an embodiment, the method comprises determining the base concentration in the IL/$H_2O$ mixture utilizing a non-linear relationship between peak intensities and the base concentration.

In an embodiment, the non-linear relationship is described with a power law model.

In an embodiment, using a quantitative calibration model involves using multivariate calibration.

In an embodiment, the multivariate calibration utilizes partial least squares (PLS) regression.

In an embodiment, the method comprises simultaneously determining (a) the acid, base and $H_2O$ content and/or (b) $H_2O$ concentration and A:B ratio in the IL/$H_2O$ mixture.

In an embodiment, the method comprises quantification of one or more ionic liquid degradation products. Said degradation products may be formed in the IL/$H_2O$ mixture, for example when the water reacts with the ionic liquid. In particular, the degradation product may be a hydrolysis product, such as 1-(3-aminopropyl)2-pyrrolidone (APP). The degradation may comprise degradation of the base of the ionic liquid. The quantification may comprise determining the concentration of the degradation product. The quantification may be performed using the quantitative calibration model with the one or more Raman spectra to quantify the one or more ionic liquid degradation products. The quantification may be performed substantially simultaneously with determining (a) the acid, base and $H_2O$ content and/or (b) $H_2O$ concentration and A:B ratio in the IL/$H_2O$ mixture. The quantification may be performed substantially in real-time, for example for monitoring and/or controlling a process involving the use of an IL/$H_2O$ mixture. The quantification may be used for quantitative monitoring of one or more degradation products for process control, for example simultaneously with A:B ratio and/or $H_2O$ content.

In an embodiment, the quantification of one or more ionic liquid degradation products involves utilizing partial least squares (PLS) regression. The quantitative calibration model may be based on PLS for the quantification of said degradation products.

In an embodiment, the quantification of one or more ionic liquid degradation products involves dividing the one or more Raman spectra into two or more subintervals. This allows a notable reduction in calibration errors and thereby improved quantification. The number of sub-intervals may be optimized for minimizing the Root Mean Square Error of Calibration (RMSEC). In some embodiments, the number of sub-intervals may be smaller than 10.

According to a second aspect, a method for monitoring and/or controlling a process involving the use of an IL/$H_2O$ mixture is disclosed. The method comprises the method according to the first aspect or any of its embodiments.

In an embodiment, the method comprises quantitative monitoring of an A:B ratio and/or $H_2O$ content for process control.

According to a third aspect, a method for the production of Lyocell-type man-made cellulosic fibers based on cellulose pulp dissolution in an IL, dry-jet wet spinning of the solution in a $H_2O$ bath and a subsequent solvent recovery step, in which the IL and $H_2O$ are separated is disclosed. The method comprises the method according to the first aspect and/or the second aspect or any of their embodiments for quantification of water and/or one or more ionic liquid components in an IL/$H_2O$ mixture.

In an embodiment, the method comprises solvent purification based on the quantification of the one or more ionic liquid degradation products. Quantification of one or more ionic liquid degradation products allows monitoring build-up of said degradation products in the solvent. Consequently, a harmful build-up of the degradation products, which may prevent or hinder the production of the fibers, may be prevented. The quantification may be used to determine, for example, how intensively purification is performed and/or how often or when purification is performed for the solvent. The purification may comprise at least partially removing and/or deactivating, which may include reverting and/or regenerating, the one or more degradation products from the solvent.

It is to be understood that the aspects and embodiments described above may be used in any combination with each other. Several of the aspects and embodiments may be combined together to form a further embodiment of the invention.

In the following, general examples are provided for answers to questions underlying the disclosure. The answers should not be considered as the only potential alternatives pertaining to the invention, instead they may be seen as generic principles, which may be utilized for describing the invention.

There is no reliable, in-line, quantitative, and fast analytical method for the simultaneous quantification of the ionic liquid components (cations and anions) and water molecules composing the liquid streams, e.g., in the Ioncell-F process. Without a continuous measurement of those molecules, the monitoring and control of the process would be very difficult.

We developed a fast and quantitative method for the simultaneous quantification of the ionic liquid components (cations and anions) and water molecules in liquid mixtures composed of water and ionic liquids.

By using the developed method, the customer can monitor and control the process in real time which is a necessity for a good and stable process operation. This process stability is a direct economic benefit, as it leads to less down-time and more uniform product quality with less rejects.

The invention may be included as a part of the patent portfolio related to the Ioncell-F technology. We sell an in-line analytical method for the monitoring and controlling the liquid streams composed of ionic liquid and water in the Ioncell-F process. The invention may also be utilized for other processes utilizing ionic liquid/water streams.

The total market for textile fibers is currently 103 Mt per year, of which 6.3 Mt is man-made cellulosic fibers. The estimated CAGR for man-made cellulosic fibers such as Ioncell-F is 7.5%. (Source: Fiber Year 2018) The customer can be either a pulp producer, a textile fiber producer or other industrial player, who is interested in adding the Ioncell fibre into their product portfolio. The invention can be also beneficial for other processes where mixtures of ionic liquid and water are applied.

To the best of our knowledge, there is no an equivalent in-line method utilized for monitoring and controlling the liquid streams comprising of ionic liquid and water.

One of the main issues associated with ionic liquids (ILs) is their recyclability. Viable recycling concepts can only be developed if one knows what is in the IL mixtures and solutions. We have shown that it is possible to quantify water and IL components in liquid mixtures using Raman spectroscopy. In this regard, we considered Raman spectroscopy as a promising analytical method for the inline monitoring and control of the Ioncell-F process. In the present application, we also push the limits of this analytical method further by extending it to more complex and realistic liquid mixtures including a degradation product, such as a hydrolysis product, for example 1-(3-aminopropyl)-2-pyrrolidone (APP) that can be formed upon the reaction of 1.5-diazabicyclo[4.3.0]non-5-ene (DBN) with water. Quantifying the degradation product, such as APP, is important in order to measure the extent of the hydrolysis reaction and apply the right corrective measures to reverse the reaction and maintain the process within the optimal working conditions. Thus, the simultaneous quantification of the four components (acetic acid, base such as DBN, degradation product such as APP, and water) in liquid streams is investigated using Raman spectroscopy. The liquid streams may be liquid streams of the Ioncell-F process. The sensitivity of the Raman method in quantifying the degradation product such as APP is also highlighted in comparison with refractometry, which is widely applied to measure IL concentration in aqueous mixtures. Finally, we propose simple modifications on the multivariate partial least square regression model based on a variable selection algorithm to enhance the accuracy of the predicted calibration values.

Process analytical technology (PAT) is increasingly adopted for inline analysis and process control. According to Kuppers et al., the advantages of integrated process analysis and control comprise a better control over the process, safer operations, and significant economic advantages due to better product quality and short troubleshooting delays (Kueppers and Haider 2003).

For process control in industrial settings, waiting times of a few hours for an accurate and precise laboratory analysis are unacceptable. Fast and accurate feedback mechanisms are needed to avoid the production of inferior and substandard products during the analytical delay time. The combination of spectroscopy and chemometrics is ideal for such a situation where a compromise between the delay and accuracy is desired. Some of the accuracy and precision of the laboratory method is sacrificed for getting fast answers that can be used to monitor and control the process continuously (Geladi et al. 2004). With this regard, Raman spectroscopy is increasingly considered as method of choice for a fast, multi-component inline quantitative analysis, for realtime process monitoring and control (Cooper 1999).

Indeed, a single fast-acquired Raman spectrum, with its well-resolved spectral features, can provide a large amount of information about a sample. The proportional relationship between the Raman scattering intensity and analyte concentration is the basis for most of the quantitative analyses done using Raman spectroscopy (Smith and Dent 2004; Larkin 2011).

In a multicomponent system, quantitative Raman analysis relies on the principle of linear superposition: the Raman spectrum of a mixture is equal to the weighted sum of the Raman spectra of the components present in the mixture (Pelletier 2003). The attractiveness for multi-component analysis using Raman spectroscopy is reinforced by the absence of optical coherence between components in the sample, which means that the Raman scattering by one component in the sample does not influence the Raman scattering of another component (Pelletier 2003). Interference can only occur when the absorption spectrum of one or more components significantly affects the transmission of excitation or Raman scattered light to or from the target analyte. Further, possible changes in the interactions between the analytes upon changing their relative concentrations may alter their respective peak shape and intensity in the spectrum (Kauffmann and Fontana 2015).

From the perspective of process digitalization, real-time monitoring and control, we have shown that Raman spectroscopy is a very promising analytical tool for the Ioncell-F process (Guizani et al. 2020). Combining Raman spectroscopy and chemometrics would allow a real time quantification of the ionic liquid (IL), such as a protic liquid, for example 1.5-diazabicyclo[4.3.0]non-5-enium acetate [DBNH] [OAc], and water in the process liquid streams.

Nevertheless, the liquid stream composition may change as the ionic liquid can undergo a degradation, such as a reversible hydrolysis, into a degradation product, such as 1-(3-aminopropyl)-2-pyrrolidone (APP) which also forms 3-(aminopropyl)-2-pyrrolidonium acetate ([APPH] [OAc]) with acetic acid.

The formation of a degradation product, such as APP, in the liquid streams may lower or even suppress the cellulose dissolution ability of the IL and ultimately lead to the irreversible formation of a reaction product, such as APPAc. Recently, Hyde and coworkers showed that the hydrolysis reaction could be avoided by controlling the pH (Hyde et al. 2019). Limiting the hydrolysis reaction is thus possible but will not be discussed in detail in this application. The process viability is therefore dependent on the constant monitoring of degradation product formation and on reversing the degradation reaction, such as hydrolysis, when it occurs. Hence, the inline Raman method may include determining the degradation product concentration in the process streams. For example, the any disclosed method may include determining a degradation product concentration, such as a hydrolysis product concentration, when an IL prone to degradation, such as hydrolysis, is used. The IL may be a protic IL, such as non-imidazolium based protic IL. The degradation product may be determined in the process streams.

Since DBN and APP show structural differences, which would lead to distinct scattering signals, we hypothesized that the Raman quantitative analytical method pertaining to DBN could be extended to mixtures containing APP. Hence, we also investigate the potential of Raman spectroscopy for the quantification of a more challenging and complex multicomponent mixture of DBN, APP, acetic acid (AcOH) and $H_2O$. We also explore a simple modification of multivariate regression model algorithm using variable selection in order to improve the model prediction performances.

With short analytical delays and acceptable accuracy in determining the expectable liquid stream composition, Raman spectroscopy shows significant potential for process monitoring and control, in particular for the Ioncell-F process. Concentrations of water, IL components and degradation product in the liquid streams could be determined in real time using adequate Raman in-situ probes. The real-time information can be used to monitor and control the process operations.

Compared to the more widely applied refractometry for measuring aqueous IL concentration, Raman spectroscopy reveals a much better sensitivity in detecting the IL degradation products and shows hence a clear advantage. This study further confirmed that the combination of Raman spectroscopy and chemometrics opens the door for reliable monitoring and efficient control of a potential wide range of IL-based processes.

BRIEF DESCRIPTION OF THE DRAWINGS

The accompanying drawings, which are included to provide a further understanding and constitute a part of this specification, illustrate examples and together with the description help to explain the principles of the disclosure. In the drawings.

Figure 1:
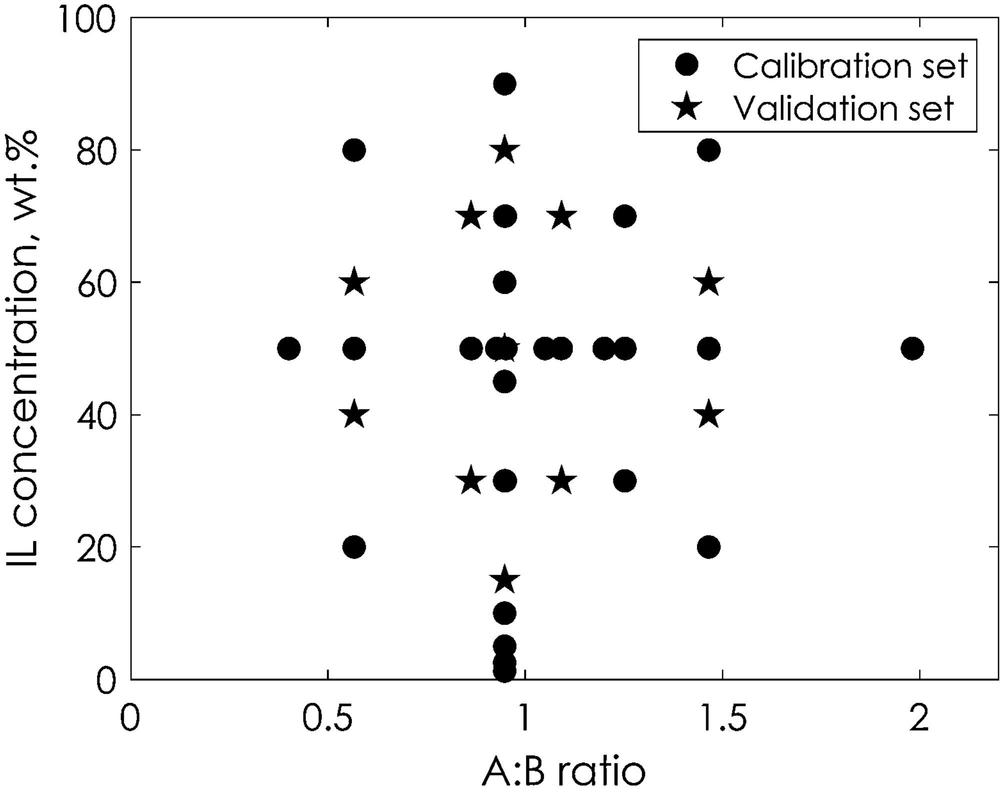
FIG. 1 illustrates samples of IL/$H_2O$ mixtures according to an example.

Like references may be used to designate equivalent or at least functionally equivalent parts in the accompanying drawings.

DETAILED DESCRIPTION

The detailed description provided below in connection with the appended drawings is intended as a description of examples and is not intended to represent the only forms in which the example may be constructed or utilized. However, the same or equivalent functions and structures may be accomplished by different examples.

The disclosed methods may be used for an ionic liquid. In an embodiment, the ionic liquid is or comprises a protic ionic liquid. In an embodiment, the ionic liquid is or comprises a non-imidazolium and/or a superbase-based ionic liquid. In an embodiment, the ionic liquid is or comprises an amidine- or guanidine-based protic ionic liquid. In an embodiment, the ionic liquid is or comprises a DBN-based and/or TBD-based ionic liquid.

The DBN-based ionic liquid may comprise a 1,5-diazabicyclo[4.3.0]non-5-enium cation of the formula (I), (I)

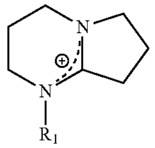

wherein $R_1$ is selected from the group consisting of hydrogen, linear and branched $C_1$-$C_6$ alkyl, $C_1$-$C_6$ alkoxy, $C_1$-$C_{10}$ alkoxyalkyl and $C_{6-18}$ aryl groups, which optionally are substituted with one or more substituents selected from hydroxy and halogen, and an anion selected from halides, such as fluoride, chloride, bromide and iodide; pseudohalides, such as cyanide, thiocyanide, and cyanate; a carboxylate, preferably formate, acetate, propionate, or butyrate; an alkyl sulphite, an alkyl sulphate, a dialkyl phosphite, a dialkyl phosphate, a dialkyl phosphonites, and a dialkyl phosphonate.

The DBN-based ionic liquid may also comprise a 1,5-diazabicyclo[4.3.0]non-5-enium cation of formula (I) above, where $R_i$ is H, and the anion is a carboxylate anion, preferably formate, acetate, propionate or butyrate.

In an embodiment, the DBN-based ionic liquids is or comprises [DBNH] [$CO_2$Et] and/or [DBNH] [OAc].

The TBD-based ionic liquid may comprise a cationic 1,5,7-triazabicyclo[4.4.0]dec-5-enium [TBDH]+moiety and an anion selected from the group according to Formula a), Formula b) and Formula c), a)

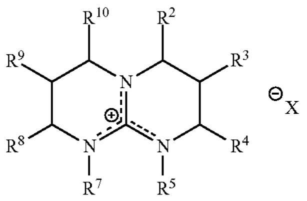

-continued b)

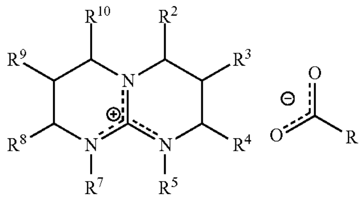

c)

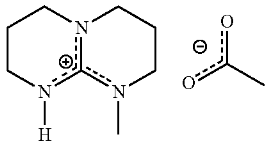

wherein each of R, R2, R3, R4, R5, R7, R8, R9 and R10 is H or an organyl radical and X— is selected from the group consisting of halides, pseudohalides, carboxylates, alkyl sulphite, alkyl sulphate, dialkylphosphite, dialkyl phosphate, dialkyl phosphonites and dialkyl phosphonates.

All embodiments may be used in any combination with each other.

1. Materials and Methods

1.1. Materials

Samples of 1.5-Diazabicyclo[4.3.0]non-5-ene (DBN) (CAS no. 3001-72-7; purity ≥99.0% in mass) and acetic acid (HOAc) (CAS no. 64-19-7; purity 299.8% in mass) were purchased from Fluorochem and Sigma-Aldrich, respectively, and were used without further purification.

1.2. Sample Preparation

1.2.1. Water-Free ILs

[DBNH] [OAc] was prepared by the slow and controlled addition of an equimolar amount of HOAc to DBN. The mixture was stirred and cooled in the beginning at 25° C. to divert the exothermic reaction enthalpy. When approaching the equimolar amounts in the mixture, the system was heated at 70° C. to avoid the crystallization of the IL. The system was kept for another hour at this temperature under mixing to ensure the reaction runs until completion. The water content of the synthesized IL is lower than 0.5 wt. %.

This IL sample was analyzed by $^1$H NMR to determine its A:B ratio. The other samples were prepared by mixing the initial IL with known amounts of HOAc or DBN to reach the target A:B ratio. These samples were then mixed for homogenization and analyzed again by $^1$H NMR for final determination of A:B ratio. The prepared samples were in the A:B molar ratio range of 0.4-1.98.

1.2.2. IL/$H_2O$ Mixtures

IL/$H_2O$ mixtures were prepared by dilution of the water-free IL samples with water. A 1 mg precision electronic scale was used during the dilution process to adjust the IL/$H_2O$ mixture to the target concentration. The covered IL concentration range was large enough to simulate concentrated and diluted samples (1.25-90 wt. % of IL in IL/$H_2O$ mixtures) with different molar A:B ratios (0.4-1.98). The IL/$H_2O$ mixtures were divided into calibration and validation sets for the model calibration and validation procedures. As each sample can be represented by its A:B ratio and IL concentration, the sample subsets are shown in FIG. 1.

FIG. 1 illustrates samples of IL/$H_2O$ mixtures according to an example.

1.3. 1H NMR Measurements

Water-free IL samples were characterized by $^1$H NMR. Samples were loaded into standard 5 mm NMR tubes and dissolved in DMSO-d6. The spectra were acquired at 23° C. using a Bruker 400 MHz Ultra Shield NMR instrument (Bruker, Billerica, Massachusetts, USA). NMR spectra were collected following the standard zg30 sequence with eight transients and an acquisition time of 2.56 s. All of the spectra are referenced to tetramethylsilane. The ACD/1D NMR Processor software was used for the treatment of the raw data. The A:B ratios were calculated by considering the ratio between the area of peaks related to the acid and to the base, respectively.

1.4. Raman Spectra Acquisition

The samples were analyzed with an Alpha 300 R confocal Raman microscope (WITec GmbH, Germany) at ambient conditions. Nearly 100 μL of the IL/$H_2O$ mixture were spread on a microscope concavity slide and covered with a cover glass. The Raman spectra were obtained by using a frequency doubled Nd:YAG laser (532.35 nm) at a constant power, and a Nikon 20× (NA=0.95) air objective. The Raman system was equipped with a DU970 N-BV EMCCD camera behind a 600 lines/mm grating. The excitation laser was polarized horizontally. After fixing the focus using the microscopy mode, each single spectrum was acquired as an average of 32 scans with an integration time of 0.1 s/scan. The baseline of the spectra were corrected with WITec Project 1.94 (WITec GmbH, Germany) using a 2$^{nd}$ order polynomial equation.

In total, 75 spectra were collected, with at least two replicates for each sample. The calibration set comprises 54 spectra and the validation set comprises 21. The samples and spectra of the two sets were prepared and collected independently on different days.

1.5. Calibration Methods Development for the Determination of the Acid, Base and $H_2O$ Concentration in the IL/$H_2O$ Mixtures

1.5.1. Univariate Calibration

Univariate calibration is the simplest approach to build a quantitative calibration model. It is based on finding relationships between single Raman spectral variables (peak intensity, peak area, peak shift) and the analyte concentration. A Matlab® (The Mathworks, Inc. Natick, Massachusetts, United States) routine was created for the Raman spectra analysis, correlation identification and calculation of the calibration models parameters.

The fit quality is assessed through the coefficient of determination ($R^2$) and the Root Mean Square Error of Calibration (RMSEC) and Prediction (RMSEP) which are expressed as:

$$RMSEC = \sqrt{\frac{\sum_{i=1}^{N}\left(y_i^{cal} - \hat{y}_i^{cal}\right)^2}{N}},$$

where $y_i^{cal}$ and $\hat{y}_i^{cal}$ denote the measured and predicted values, respectively, and N the number of samples in the calibration data set, and $$RMSEP = \sqrt{\frac{\sum_{i=1}^{K}\left(y_i^{val} - \hat{y}_i^{val}\right)^2}{K}},$$

where $y_i^{val}$ and $\hat{y}_i^{val}$ denoted the measured and predicted values, respectively, and κ the number of samples in the validation data set.

Although univariate calibration can work successfully in some cases, it sometimes fails in giving good results when dealing with complex Raman spectra that show for instance overlapping bands or unexpected shifts over the calibration range. In those cases, a multivariate approach would be more appropriate for calibration model building [19] [20].

1.5.2. Multivariate Calibration: Partial Least Squares Regression (PLS)

When building calibration models using spectroscopic data and multivariate analysis, one usually encounters two main problems: there are typically much more spectral variables than samples, and there is a high variable collinearity encountered in most of the spectral data. This makes classical multiple linear regression (MLR) based on the original spectral variables either impossible or highly unstable.

A robust alternative to MLR is Partial Least Squares (PLS) regression. PLS projects data (spectral intensities in our case) in a new space with a smaller number of new variables. Those new variables are called components or Latent Variables (LVs). PLS calculates the LVs in a way that the covariance between the X block (spectral intensities), and the Y block (concentration of the different species) is maximized.

The LVs are mutually orthogonal, which suppresses problems related to matrix inversion when calculating the model coefficients. The reduction of the space dimension in addition to the mutual orthogonality of the LV makes PLS especially suitable for building predictive models out of spectroscopic data. A very good explanation of the principles of PLS is given in reference [21].

During the calibration procedure, the collected spectra are placed as rows in a X matrix (independent block), with n rows and k columns. Each row represents a spectrum and each column a single wavelength. The variables that we aim to predict are placed in a Y matrix (dependent block), with n rows and m columns. Each row represents one sample and each column a single variable.

Briefly, in PLS there are outer relations for which the X and Y blocks are decomposed into scores and loadings matrices:

$$X=TP'+E$$

$$Y=UQ'+F^*$$

Where:

- T and U represent respectively the score matrices for the X and Y blocks.
- P' and Q' represent respectively the score matrices for the X and Y blocks.
- E and F* represent respectively the matrices of residuals for the X and Y blocks after the projection onto a defined number of LV.

There is also an inner relation between the scores, linking both blocks $$U=BT,$$

where B is the matrix containing the regression vectors. A mixed relation can be written as:

$$Y=TBQ+F,$$

where ||F|| is to be minimized.

This mixed relation ensures the ability to use the model parameters for future prediction from a test set.

In the present study, the X block contains the Raman spectra of each sample and the Y block the weight fractions of acid, base, and $H_2O$ in each sample.

The number of LVs, the fit quality, and model validation were investigated through the evaluation of the $R^2$ coefficient, RMSEC and RMSEP.

Data analysis and model building were performed with Matlab® and the Matlab® PLS Toolbox (Eigenvector Research, Inc. Manson, United States) software packages.

2. Results and Discussion

2.1. $^1$H NMR of Water-Free IL Samples

Figure 2:
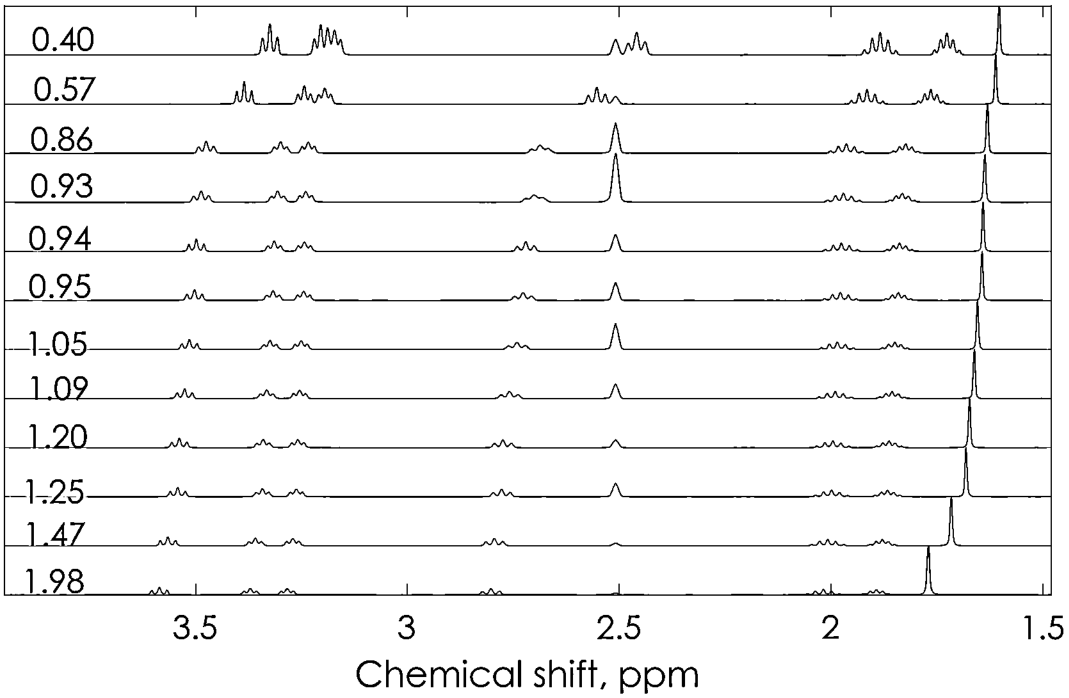
FIG. 2 illustrates NMR spectra of the waterfree IL with different A:B ratios according to an example (A:B ratio is indicated on the left side of the figure for each sample)

The NMR spectra of the water-free ILs as well as the corresponding A:B ratio are shown in FIG. 2. The DMSO-$d_6$ singlet is visible at ≈2.5 ppm. The singlet observed in the range of ≈1.6-1.75 ppm corresponds to the protons of the methyl groups in the acetic acid/acetate molecules. The rest of the multiplets correspond to the different protons of the base and its protonated form. Details about the acid and base proton chemical shifts are indicated in the supplementary materials.

As expected, only mixed peaks can be observed instead of peaks that represent molecular and ionic species separately. For the rapid exchange system, the observed $^1$H chemical shift is assumed to be the weighted average of the molecular and ionic species.

One can notice a shift of the of the different peaks related to HOAc, DBN, and their ionized forms to the high ppm values when increasing the A:B ratio. These shifts can be directly linked to the different shielding/deshielding effects experienced by the protons when changing the A:B ratio.

FIG. 2 illustrates NMR spectra of the waterfree IL with different A:B ratios according to an example (A:B ratio is indicated on the left side of the figure for each sample).

For instance, when the A:B ratio is increased, protons belonging to the acid methyl group (1.6-1.8 ppm) are shifted downfield. This is probably due to a higher hydrogen-bonding network between these protons and the oxygen atoms of the carboxylate group in neighboring free acetic acid molecules. This reduces the shielding around these protons and make them resonate at higher frequency.

The position of the methyl group singlet is linearly correlated to the A:B ratio, with a noticeable increase of the slope starting from A:B=0.85 denoting higher proton deshielding beyond this value. Similar linear relationships and slope change over the investigated A:B range were found for the equivalent protons bonded to C3 and C9 in DBN/DBNH+. The change of slopes is, however, different. The slopes were pronounced below A:B=1.1 and decreased markedly beyond this value, which means that the proton deshielding decreases markedly beyond this value. These results are illustrated in the supplementary materials. The different chemical shifts can be used to calculate the IL ionicity as explained in [22].

The A:B ratios were calculated by taking the ratio of the integral area of methyl group singlet (acid) to the sum of the integrated areas of the different multiplets (base). The area of the triplet observed in the range of =3.27-3.95 ppm, corresponding to the two hydrogen bonded to C9 was taken as a reference. The estimated relative error for the calculation of the A:B ratio was less than 5%.

2.2. Raman Spectroscopy

2.2.1. Raman Spectra of the Acid, Base, and IL

Figure 3:
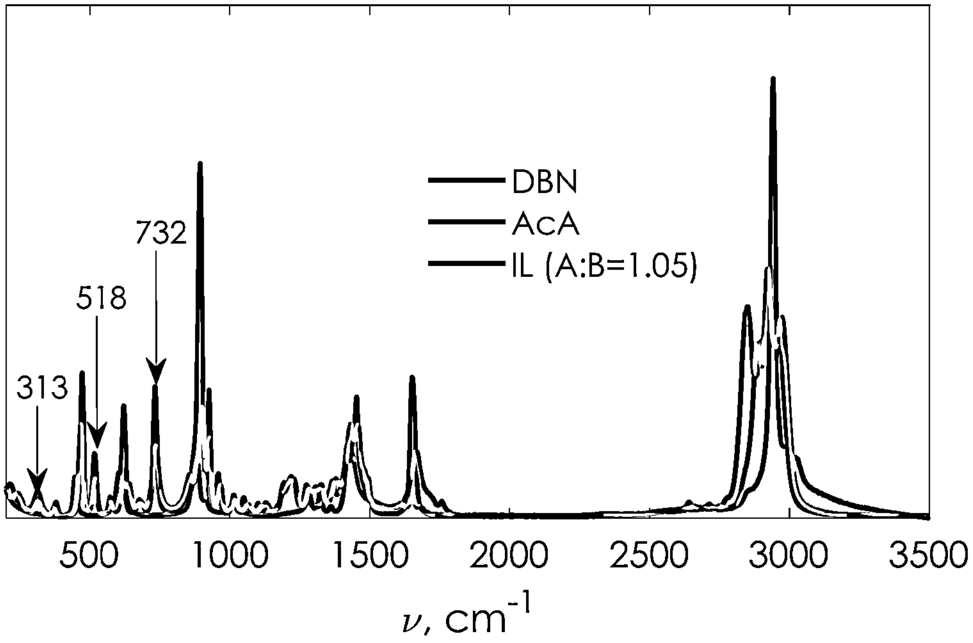
FIG. 3 illustrates Raman spectra of DBN, HOAc and the water-free ILs according to an example (A:B=1.05)

The area normalized Raman spectra of DBN, HOAc and IL (A:B=1.05) are presented in FIG. 3. In the HOAc spectra, the two prominent peaks at 895 $cm^{-1}$ and 2950 $cm^{-1}$ are ascribed, respectively, to the C—C and C—H stretching vibrations. The medium intensity band at ≈1665 $cm^{-1}$ is attributable to the C═O stretching vibration [23].

FIG. 3 illustrates Raman spectra of DBN, HOAc and the water-free ILs according to an example (A:B=1.05).

To the best of our knowledge, the assignment of the specific Raman bands for DBN has not been presented in the literature. The band assignment herein is based on Raman spectral tables [24] [25]. The peak at 313 $cm^{-1}$ and 732 $cm^{-1}$ could originate from C—C vibrations. The peak at 518 $cm^{-1}$ could be attributed to C—N vibrations. The peak at 1650 $cm^{-1}$ could be ascribed to C═N stretching, while the peaks at 1452 $cm^{-1}$ and 2850 $cm^{-1}$ could be ascribed to $CH_2$ vibrations. Interestingly, the peaks at 313 $cm^{-1}$, 518 $cm^{-1}$, and 732 $cm^{-1}$ do not overlap with peaks of HOAc, and would probably be good candidates to build a calibration model.

The Raman spectra of IL (A:B=1.05) display a complex pattern in which we can distinguish some features from the spectra of HOAc and DBN, respectively. One can note, for instance, that the peaks at 313, 518, and 732 $cm^{-1}$ show a decrease in intensity compared to the pure base without any noticeable change in the shape or in the peak position, which confirms again their potential use for calibration. Some other overlapping peaks, for instance between 800-1000 $cm^{-1}$ or between 2800-3200 $cm^{-1}$, are more complex to interpret and results from the overlaps/shifts of the peaks from HOAc and DBN. A noticeable shift of the DBN peak related to —$CH_2$ vibrations from 2850 $cm^{-1}$ in the pure base to 2880 $cm^{-1}$ in the IL is observed. Ionization and interactions between the molecular and ionized HOAc and DBN are probably behind those shifts.

2.2.2. Raman Spectra of Water-Free A/B Mixture with Excess of Base or Acid

Figure 4:
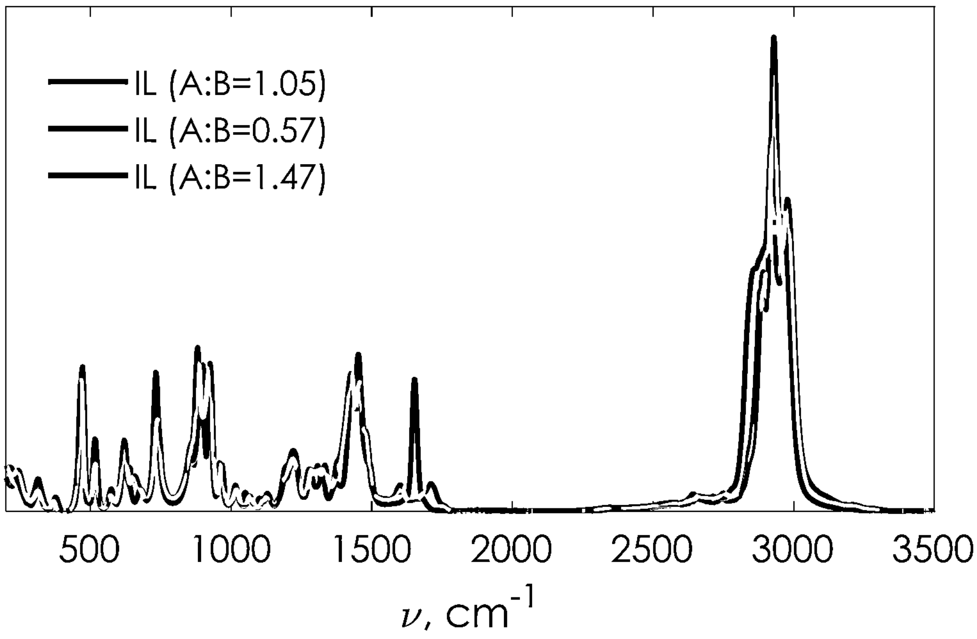
FIG. 4 illustrates Raman spectra of water-free IL with different A:B ratios according to an example.

FIG. 4 shows the Raman spectra of the IL in nearly equimolar amounts of acid and base and in an excess of base or acid. We already mentioned that the peak intensities at around 1650 $cm^{-1}$ in the HOAc and DBN spectra decreased drastically in the nearly equimolar IL. When deviating from the equimolar composition, we can observe that the 1650 $cm^{-1}$ peak intensity increases substantially when there is an excess of DBN, while in excess of acid, we can notice the presence of a peak at 1700 $cm^{-1}$. Based on those observations, we can conclude with a greater certainty that these peaks are related to the C═N and C═O vibrations in the non-ionized DBN (excess of base) and HOAc (excess of acid) forms.

Indeed, for the nearly equimolar composition, once the proton exchange occurs when the acid and base are mixed, a great proportion of the molecules become ionized, the two double bonds become delocalized, and no "real" C═O or C═N vibration can be seen in the Raman spectra of the IL. When there is an excess of acid or base, those bands are more prominent due the presence of the neutral molecules.

It is also worth-mentioning here that in the case of protic IL like [DBNH] [OAc], a chemical equilibrium takes place between ionized and neutral species (the equilibrium constant is directly linked to the so called ionicity of the IL). This may then explain why the band intensities of the double bonds do not vanish completely even in nearly equimolar composition (presence of neutral species) [4].

FIG. 4 illustrates Raman spectra of waterfree IL with different A:B ratios according to an example.

The excess of base or acid in the mixtures affects also the spectrum in the high wave number region (2200-3200 $cm^{-1}$). At low A:B ratio (excess base), the area in the range 2800-2900 $cm^{-1}$ increases with the appearance of a shoulder at low wave numbers, and most probably related to molecular vibrations in the free base, while at high A:B ratios the area in the range 3000-3100 $cm^{-1}$ increases mostly due to the presence of the molecular acid.

2.2.3. Effect of Water on the Raman Spectra of ILs as a Function of the A:B Ratio So far, we showed that an excess of acid or base induces noticeable changes in the Raman spectra of A/B mixtures. In this section, we discuss the effect of water dilution of IL. The spectra of the different A:B ratio water-diluted IL samples (50 wt. % of water) are shown in FIG. 5.

Dilution with water caused indeed noticeable changes in the Raman spectra compared to the water-free ILs. A broad band ascribed to the different O—H vibrations modes in the water molecule appeared in the wave number range of 3000-3700 $cm^{-1}$, in addition to another peak ascribed to a bending vibration mode of water near to 1595 $cm^{-1}$ [26]. The peak at around 1650 $cm^{-1}$ attributed to the C═N vibration in the free base drastically decreased in the presence of water (probably due to ionization) and is only visible for samples with low A:B ratios. The peaks at 1600 $cm^{-1}$ and 1700 $cm^{-1}$ related to the free acid molecules are also visible in diluted samples with high A:B ratios. Here also, chemical equilibria define the ionization extent of the different molecules.

Figure 5:
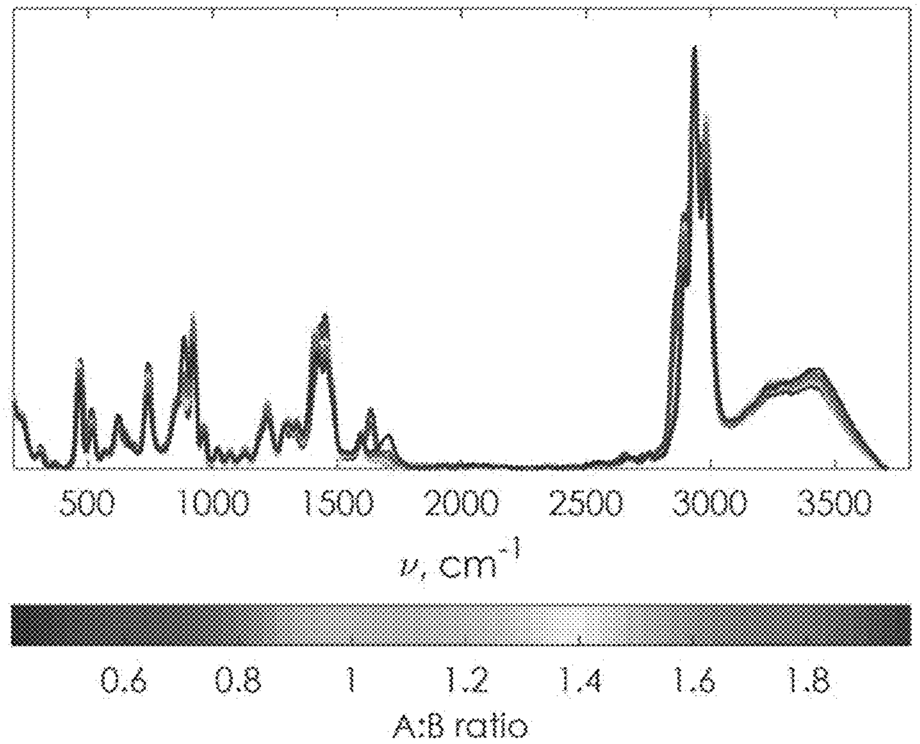
FIG. 5 illustrates area-normalized Raman spectra of the 50 wt. % water diluted IL samples according to an example (The color code is related to the A:B ratio)

FIG. 5 illustrates area-normalized Raman spectra of the 50 wt. % water diluted IL samples according to an example (The color code is related to the A:B ratio).

Drastic changes were also reported for the IR and NMR spectra of Imidazolium-based ionic liquids having different anions upon the introduction of water due to interactions between the IL and $H_2O$ molecules [27].

2.2.4. Raman Spectra of the IL/Water Mixtures

Figure 6:
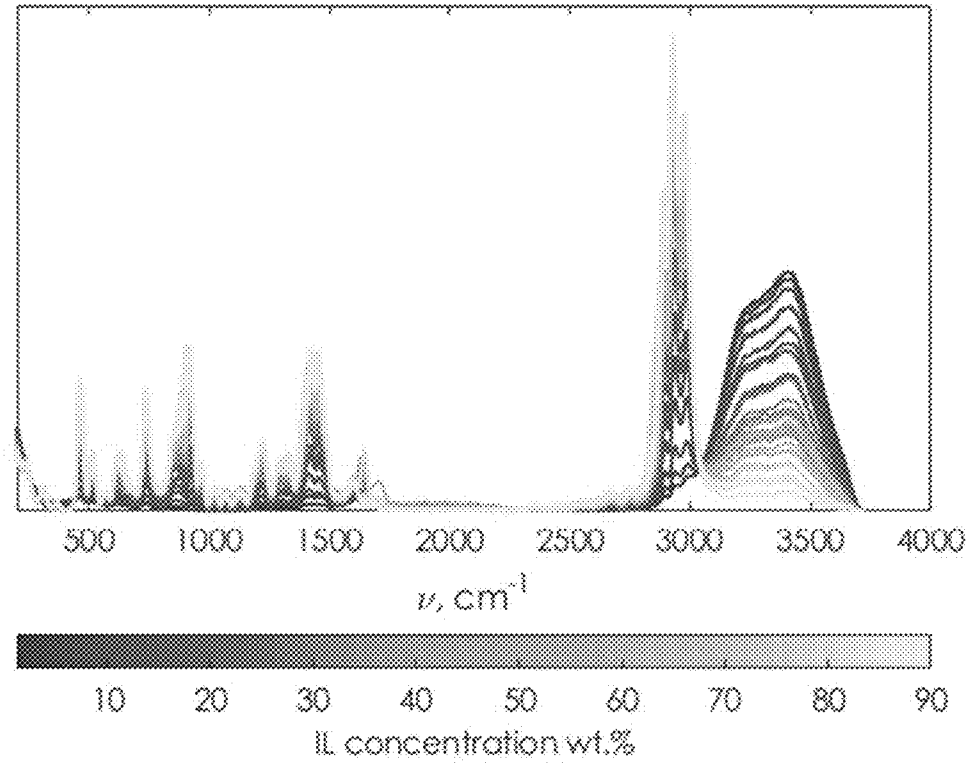
FIG. 6 illustrates area-normalized Raman spectra of the different IL/$H_2O$ solutions according to an example (The color code reflects the IL concentration in the IL/$H_2O$ mixture)

The Raman spectra of the different IL/$H_2O$ samples are shown in FIG. 6. As depicted in this figure, the intensity of the broad peak in the wave number range of 3000-3700 $cm^{-1}$ ascribed to the different O—H vibrations modes in the water molecules increased with the dilution factor, while the scattering intensity from the acid and base molecules/ions in the IL (practically all the remaining spectral bands) decreased. This was expected since the Raman scattering intensity is proportional the concentration of the scattering molecules.

Although the presence of water caused noticeable changes in the Raman spectra of IL, its scattering does not noticeably interfere with the scattering resulting from the IL molecules.

FIG. 6 illustrates area-normalized Raman spectra of the different IL/$H_2O$ solutions according to an example (The color code reflects the IL concentration in the IL/$H_2O$ mixture).

2.2.5. Univariate Calibration Approach for the Determination of $H_2O$ Concentration in IL/$H_2O$ Mixtures To predict the $H_2O$ concentration in a $H_2O$/IL mixture, the intensity variation in the range of 2200-3800 $cm^{-1}$ can be exploited. Although there is a small overlap between the peaks ascribed to IL and $H_2O$ in the of 3000-3200 $cm^{-1}$ region, the respective signals are still relatively well separated.

We developed a quite simple method for the calibration. In our spectral treatment procedure, the spectral range was first narrowed to the 2200-3800 $cm^{-1}$ region. The raw spectra were then area-normalized. The peak areas related to IL and $H_2O$ are defined as follows:

$$IL_{peak\ area}=\int_{2200}^{3010} Id\theta$$

$$H_2O_{peak\ area}=\int_{3010}^{3800} Id\theta$$

Figure 7:
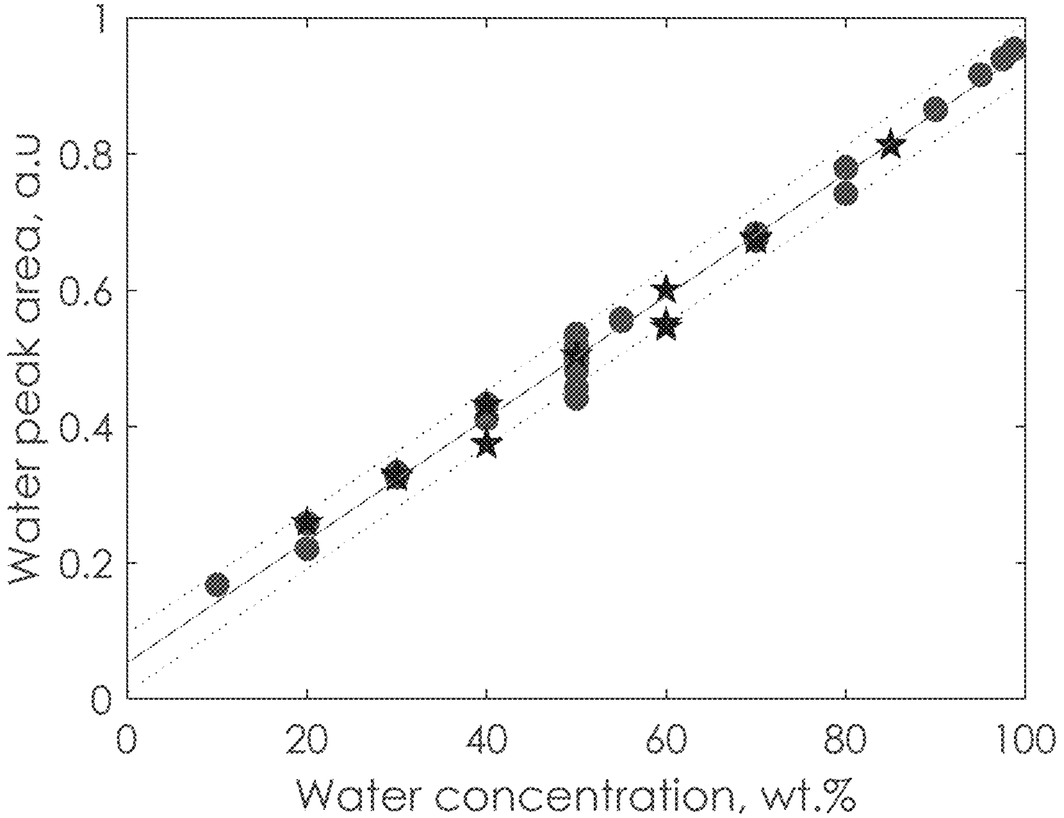
FIG. 7 illustrates integral area of the Raman scattering intensity in the 3010-3800 $cm^{-1}$ region Vs water concentration according to an example (Blue circles: calibration data set. Black stars: validation data set. Solid lines: calibration model. Dashed lines: 95% confidence interval limits)

The graphical representation of the $H_2O$ peak area $H_2O_{peak\ area}$ as a function of the $H_2O$ concentration is shown in FIG. 7.

FIG. 7 illustrates integral area of the Raman scattering intensity in the 3010-3800 $cm^{-1}$ region Vs water concentration according to an example (Blue circles: calibration data set. Black stars: validation data set. Solid lines: calibration model. Dashed lines: 95% confidence interval limits).

A significant linear relationship is obtained between $H_2O_{peak\ area}$ and the $H_2O$ mass fraction in the IL/$H_2O$ mixture. Some discrepancies at equivalent $H_2O$ mass fraction are observed for samples with different A:B ratios. Indeed, some of the spectral features change in the 2200-3010 $cm^{-1}$ region, especially at low and high A:B ratios as discussed previously. These variations can be seen specifically for the samples with 50 wt. % of water, were the covered A:B range was the largest one.

Altogether, these changes do not dramatically affect the model. The RMSEC and RMSEP were 2.234 wt. % and 2.257 wt. %, respectively. These values are reasonable, considering the simple procedure and the large concentration range from 10 wt. % to 98.75 wt. % of $H_2O$ content. The prediction error is comparable that reported by Viell at al. [12] who quantified $H_2O$ in $H_2O$/IL mixtures using mid-infrared (mid-IR) spectroscopy using advanced spectral treatment methods. The prediction error reported in their study was lower than 2.3 wt. % over the entire concentration range. Models parameters and fit quality metrics for the prediction of the water concentration in IL/$H_2O$ mixtures are given in Table 1.

TABLE 1

Models parameters and fit quality metrics for the prediction of the water concentration in IL/H2O mixtures.

| Raman peak range, $cm^{-1}$ | $R^2$ | RMSEC, water wt. % | RMSEP, water wt. % | Model: f(x) = ax + b<br>a | b |
|---|---|---|---|---|---|
| 3010-3800 | 0.991 | 2.234 | 2.257 | 0.008976 (0.008734, 0.009218) | 0.05309 (0.03843, 0.06774) |

2.2.6. Univariate Calibration Approach for the Determination of the Base Concentration in IL/$H_2O$ Mixtures The Raman scattering intensity from the IL components (acid and base) increases with IL concentration in the IL/$H_2O$ mixtures as depicted in FIG. 6. Some peak intensities showed very good correlations with the base concentration, specifically those at 743 $cm^{-1}$ and 2890 $cm^{-1}$. The intensities of these peaks as a function of the base concentration in the IL/$H_2O$ mixture are depicted in FIG. 8.

The relationship between the peak intensities and the base concentration is, however, not linear. The reasons behind this non-linearity over the base concentration range are not clear. Polynomial models can be used to approximate a complex nonlinear relationship, as they are just the Taylor series expansion of the unknown nonlinear function. However, we found that the observed relationships could be well described with simple power law models, which we adopted for the calibration equation.

Figure 8:
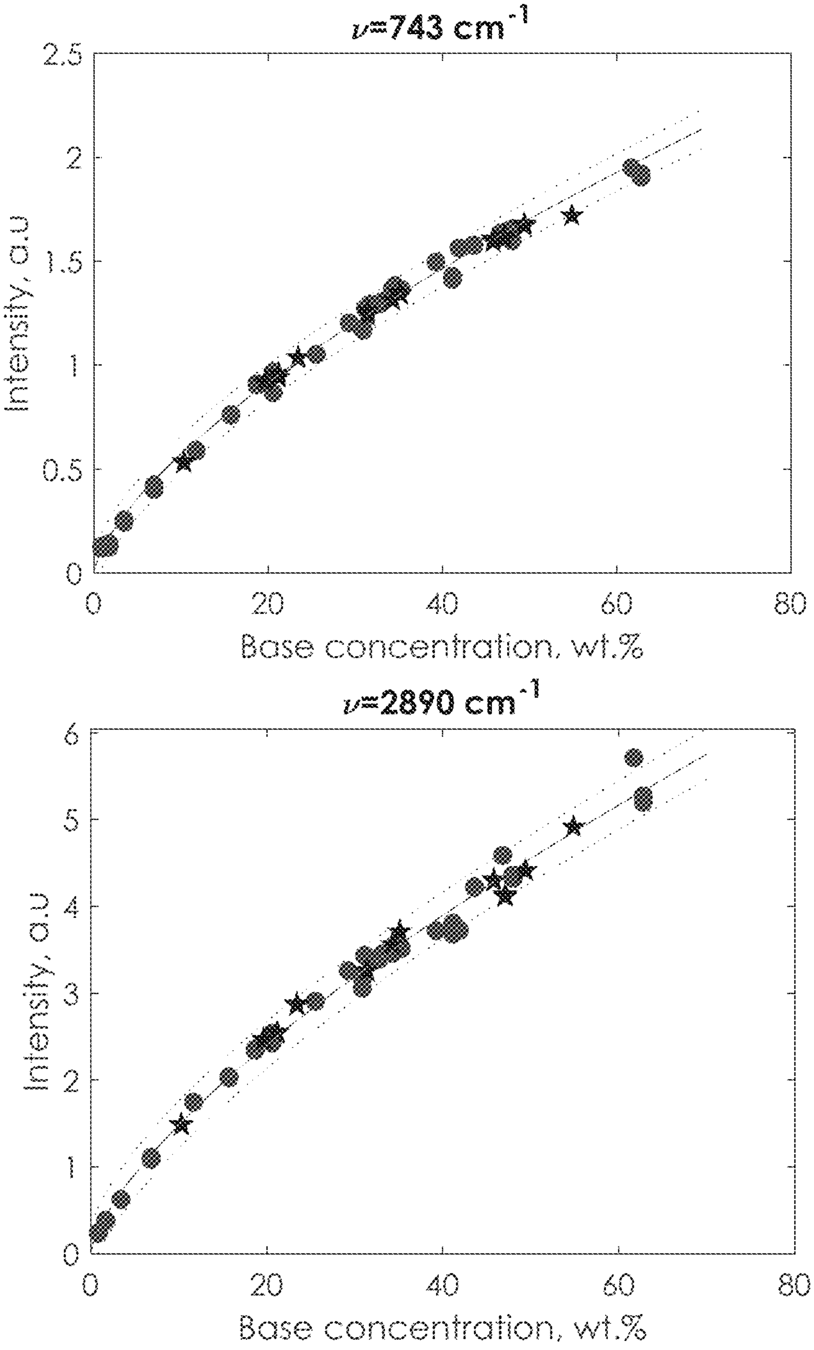
FIG. 8 illustrates evolution of peak intensities at 743 $cm^{-1}$ and 2890 $cm^{-1}$ as a function of the base concentration in the IL/$H_2O$ mixtures according to an example (Blue circles: calibration data set. Black stars: validation data set. Solid lines: calibration model. Dashed lines: 95% confidence interval limits)

FIG. 8 illustrates evolution of peak intensities at 743 $cm^{-1}$ and 2890 $cm^{-1}$ as a function of the base concentration in the IL/$H_2O$ mixtures according to an example (Blue circles: calibration data set. Black stars: validation data set. Solid lines: calibration model. Dashed lines: 95% confidence interval limits).

As depicted in FIG. 8, the fit quality is relatively good over the covered base concentration range for the two peaks. The model parameters and the fit quality metrics ($R^2$, RMSEC, and RMSEP) for the prediction of the base concentration in IL/$H_2O$ mixtures are given in Table 2.

For both peaks, the RMSEC and RMSEP were lower than 2 wt. %, which is again a quite reasonable value regarding the covered range. Nevertheless, using the peak at 2890 $cm^{-1}$ would result in a better model sensitivity, as the intensity range is larger over the same covered base concentration range.

TABLE 2

Models parameters and fit quality metrics for the prediction of the base concentration in IL/$H_2O$ mixtures.

| Raman shift, $cm^{-1}$ | $R^2$ | RMSEC, Base wt. % | RMSEP, Base wt. % | Model: $f(x) = ax^b$ a | b |
|---|---|---|---|---|---|
| 743 | 0.991 | 1.566 | 1.086 | 0.1209 (0.1101, 0.1317) | 0.6763 (0.6517, 0.7008) |
| 2890 | 0.985 | 1.944 | 1.840 | 0.2992 (0.2673, 0.3311) | 0.6957 (0.6665, 0.725) |

So far, the univariate calibration showed a good potential for the quantification of water and base in IL/$H_2O$ mixtures. Nevertheless, it showed also limitations, as we were not able to predict the acid concentration in the IL/$H_2O$ mixtures using single spectral features. The acid concentration can be still obtained by difference to 100% assuming that only water, acid and base are present in the solution.

Using multivariate calibration can greatly improve the calibration model quality and performance, as it utilizes all the information in the spectra and not only focuses on a single variable. In the next section, we will discuss the potential of one of the multivariate calibration methods, namely the PLS regression.

2.2.7. PLS Regression for the Simultaneous Determination of the IL Components and $H_2O$ Content in IL/$H_2O$ Mixtures Preprocessing is a very important step when performing multivariate data analysis. In our attempts to build the PLS calibration model, we tested several spectra preprocessing methods and evaluated them in the light of the model fit quality. The retained preprocessing strategy includes base line correction, smoothing (10 points moving window), area normalization and mean centering of the raw spectra (X block). The Y block data were mean centered.

The number of the model LVs was selected based on the minimization of the RMSECV and a visual inspection of the LVs. A model with four LVs leads to a very good fitting with more than 99% of explained variance in both X and Y blocks.

Figure 9:
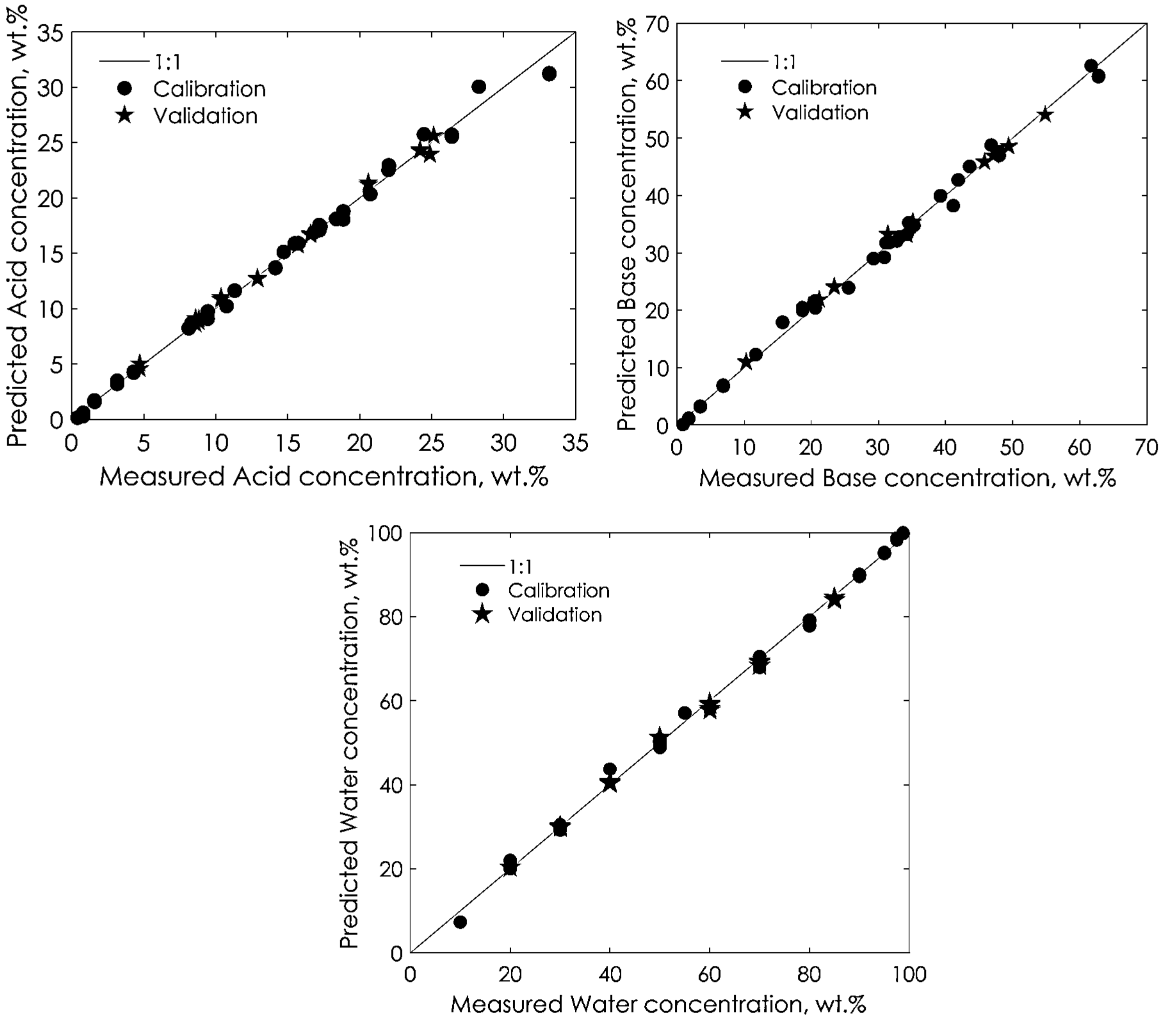
FIG. 9 illustrates prediction VS measurements plots for the acid, base, and $H_2O$ concentrations in the $H_2O$/IL mixtures according to an example.

The measured and predicted values of acid, base, and $H_2O$ concentrations for the calibration and validation data sets are shown in FIG. 9. The reader can see that the different data points are well distributed around the y=x line for both sets, which reflects a good model fit quality.

FIG. 9 illustrates prediction VS measurements plots for the acid, base, and $H_2O$ concentrations in the $H_2O$/IL mixtures according to an example.

The PLS calibration approach was clearly successful in predicting simultaneously the acid, base, and $H_2O$ contents in IL/$H_2O$ mixtures. The PLS model statistics are shown in Table 3.

TABLE 3

PLS model statistics for the prediction of acid, base, and $H_2O$ contents in the $H_2O$/IL mixtures.

| | Base, wt. % | Acid, wt. % | Water, wt. % |
|---|---|---|---|
| Concentration range | 0.86-62.81 | 0.39-33.17 | 10-97.75 |
| RMSEC, wt. % | 1.137 | 0.634 | 1.175 |
| RMSEP, wt. % | 0.908 | 0.441 | 1.037 |
| $R^2$ Calibration | 0.995 | 0.994 | 0.997 |
| $R^2$ Prediction | 0.996 | 0.996 | 0.998 |

The RMSEs are reasonable regarding the relatively wide covered range for the three variables. It has to be noted that, some of the validation set samples have acid, base, and $H_2O$ concentrations from the calibration set samples, which also reflects a good model prediction ability.

Those results are, to the inventors' best knowledge, the first in the literature to show the potential of Raman spectroscopy in combination with Chemometrics for a fast and quantitative determination of the Il components and $H_2O$ contents in IL/$H_2O$ mixtures. The applicability of this method can be extended to a wider range of processes involving IL/$H_2O$ mixtures [6]-[9].

2.2.8. Discussion on the PLS Calibration Model

The percent variance captured by the PLS regression model for the X and Y blocks are given in Table 4. LV1 and LV2 explain already nearly 99% of the variance in the data. The latent variable LV1 explains the greatest part of the variance, respectively 96.53% and 93.14% in the X and Y blocks.

TABLE 4

| Percent variance captured by the PLS regression model | | |
|---|---|---|
| Latent variable | X-Block explained variance, % | Y-Block explained variance, % |
| 1 | 96.53 | 93.14 |
| 2 | 2.31 | 2.86 |
| 3 | 0.53 | 3.24 |
| 4 | 0.38 | 0.40 |

Figure 10:
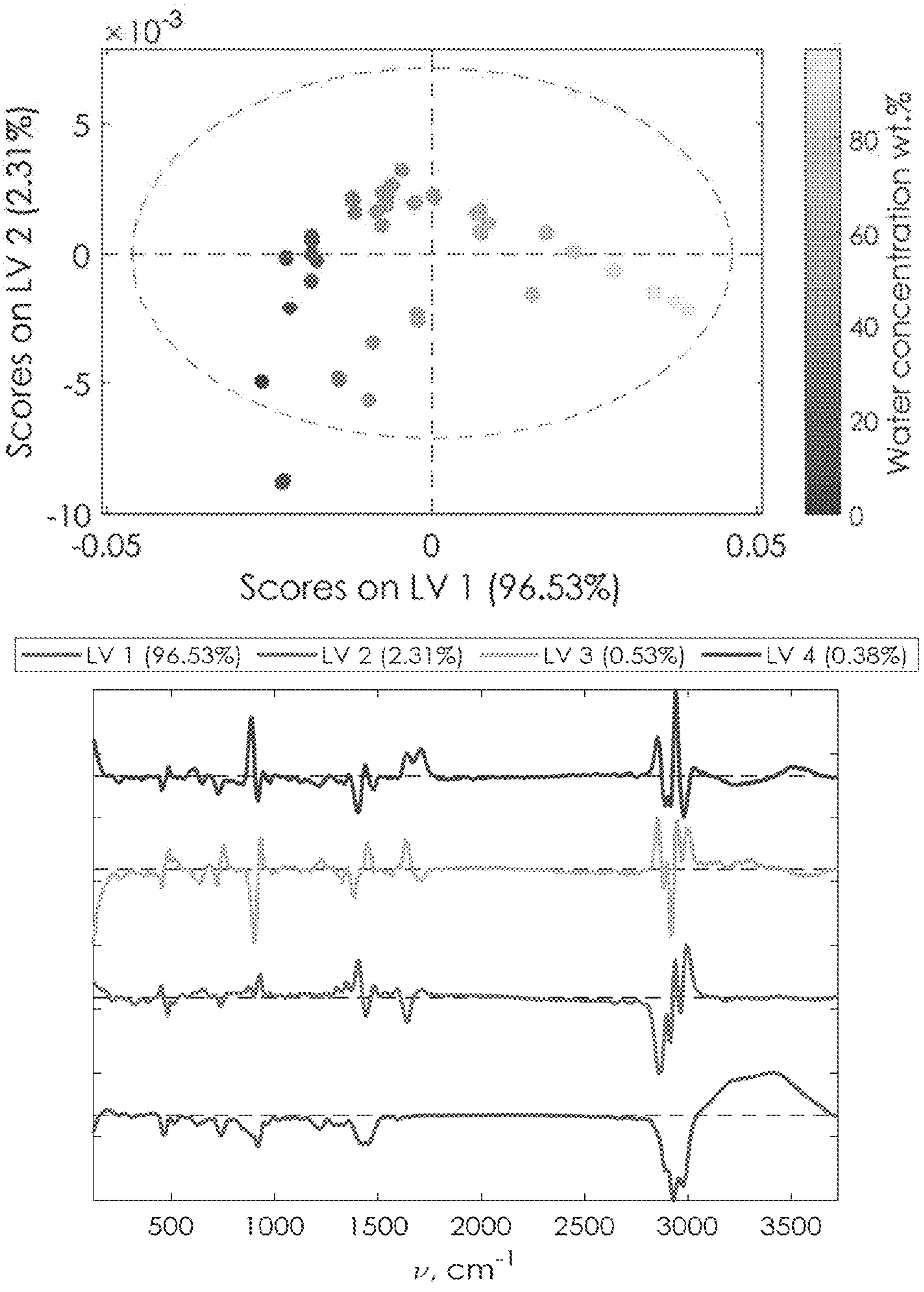
FIG. 10 illustrates score plot based on LV1 and LV2 (top) and loadings plots (bottom) for the four LVs according to an example.

The score plot based on the two first LVs as well as the loadings plots for the four LVs are shown in FIG. 10. The scores represent the coordinates of the samples in the new LV space. Samples having similar scores on the same LV are similar regarding to this LV. The corresponding loadings are used to interpret what is causing the changes in the scores and can help to elucidate the physical meaning of a particular LV. A particular loading shows the spectral features responsible for the pattern in the score plot. A high loading value for a certain wavelength (or a range of wavelengths) means that this latter contributes highly in building the latent variable.

The positive peaks in the LV1 loading spectrum show an almost complete signal of the water peak. The negative peaks constitute an almost reversed spectrum of a water-free IL. From our previous discussion, we can deduce that the LV1 is mainly explaining variation of IL (respectively water) concentration in the mixture.

This observation is confirmed when looking at the LV1-LV2 score plot, where the scores are colored with water concentration in the mixture. The samples with IL concentration close to the mean concentration (around 40 wt. %) have a score value of zero because the data are mean centered. We can see that samples with negative scores on LV1 have IL concentrations below this average, while samples with positive scores on LV1 have lower IL concentration than this average.

From the loading plot of LV2, one can already see that this latent variable is not related to $H_2O$ concentration in the sample, since the loading values for LV2 are close to zero in the wavenumber region corresponding to the O—H vibrations.

The LV2 loadings show positive and negative peaks. A closer look reveals that the negative peaks corresponds to vibrational frequencies of chemical bonds found in the base and the positive peaks occur at the vibrational frequencies of the acid (see previous discussion on peak assignment). This is confirmed on the score plot, where the samples were found to be separated along LV2 according to the A:B ratio.

The same applies for LV3 and LV4 which would explain variation in the A:B ratio rather than concentration as the respective loadings showed features related to molecular vibrations in A and B. Both LVs would also explain in part the presence of molecular acid and/or base in the sample, as some of the spectral features related to them appear on the loadings plot.

Altogether, LV2, LV3 and LV4 are related to the variation of A:B ratio in the mixture, while LV1 explains the variation of IL concentration in it.

FIG. 10 illustrates score plot based on LV1 and LV2 (top) and loadings plots (bottom) for the four LVs according to an example.

Part 2: quantification of ionic liquid degradation products and improvement of prediction performance through interval PLS.

Figure 11:
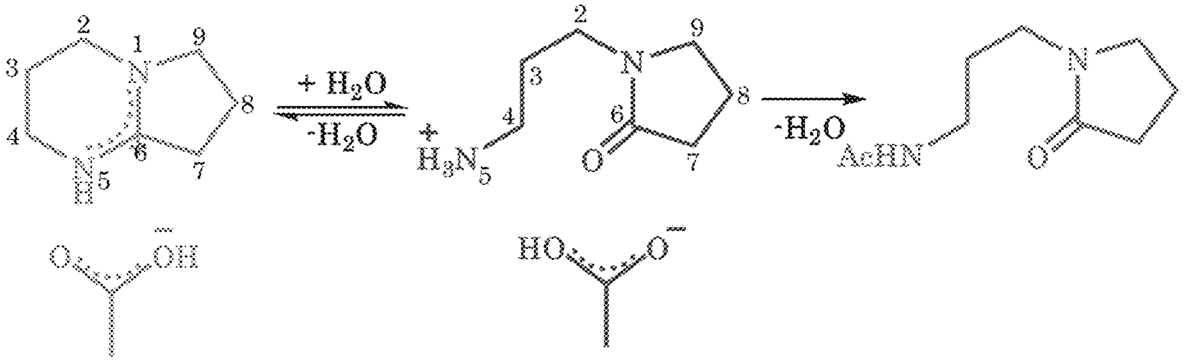
FIG. 11 illustrates [DBNH] [OAc](1) hydrolysis into [APPH] [OAc](2) and condensation into APPAc (3) according to an example.

The liquid stream composition may change as the ionic liquid, such as 1.5-diazabicyclo[4.3.0]non-5-ene (DBN), can undergo a degradation such as a reversible hydrolysis into a degradation product, such as 1-(3-aminopropyl)-2-pyrrolidone (APP) which also forms 1-(3-aminopropyl)-2-pyrrolidonium acetate ([APPH] [OAc]) with acetic acid (FIG. 11). Furthermore, [APPH] [OAc] may undergo condensation or decomposition into 1-(3-acetamidopropyl)-2-pyrrolidone (APPAc) according to the second reaction shown in FIG. 11.

FIG. 11 illustrates [DBNH] [OAc](1) hydrolysis into [APPH] [OAc](2) and condensation into APPAc (3) according to an example.

Some examples for quantifying an ionic liquid degradation product are provided. In an embodiment, the degradation product may be a hydrolysis product, such as APP, and while some of the examples are provided for this particular degradation product, any other degradation products may be applicable as well.

3. Material and Methods

3.1. Raw Materials

Samples of DBN (CAS no. 3001-72-7; purity ≥99.0% in mass) and HOAc (CAS no. 64-19-7; purity ≥99.8% in mass) were purchased from Fluorochem and SigmaAldrich, respectively, and were used without further purification.

3.2. Experimental Procedures

3.2.1. Sample Preparation

The [DBNH] [OAc] stock solution was synthetized using the procedure described in (Guizani et al. 2020). 1-(3-aminopropyl)-2-pyrrolidonium acetate ([APPH] [OAc]) was synthetized by the University of Helsinki. The stock solution of [APPH] [OAc] contained partly DBN. Both stock solutions used for the sample preparation were characterized using capillary electrophoresis, NMR and Karl Fisher titration for the determination of the initial AcOH, DBN, APP and $H_2O$ concentrations. Their specifications are given in Table 8 in the Electronic Supplementary Information (ESI).

Figure 19:
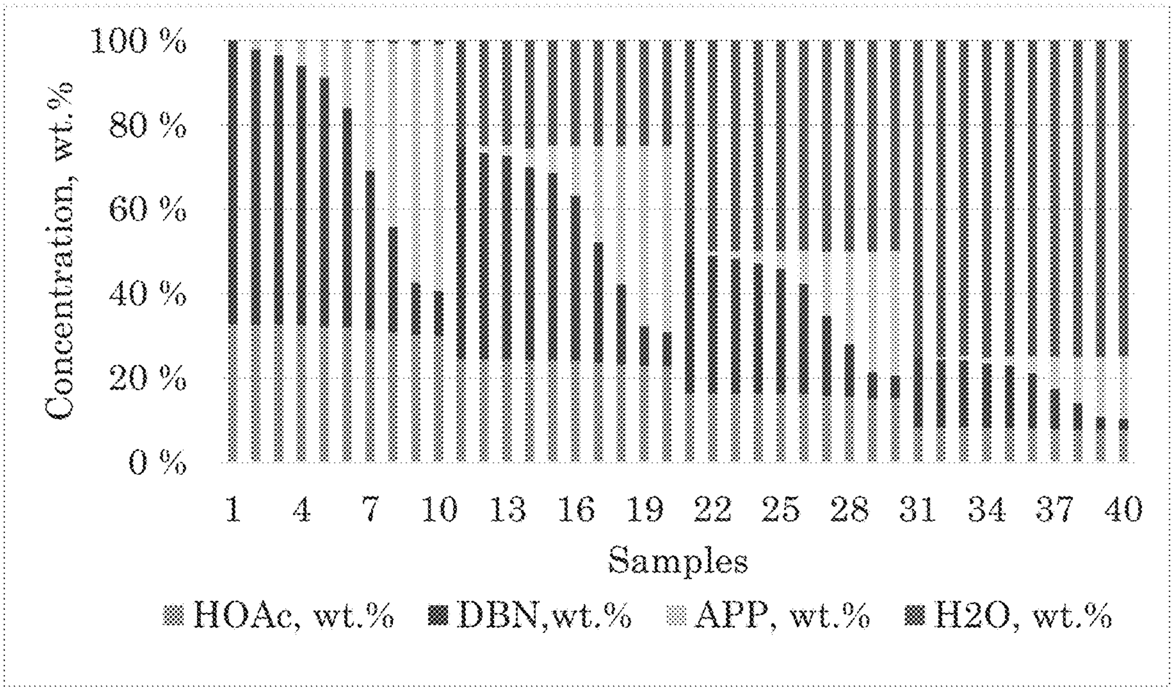
FIG. 19 illustrates sample composition according to an example.

Out of those stock solutions and distilled $H_2O$, forty samples (each weighing more than 3 g) with defined compositions were prepared gravimetrically using an electronic weighing scale with a precision of 0.1 mg. These forty samples can be classified into four categories as a function of the water contents (–0 wt. %, –25 wt. %, –50 wt. % and –75 wt. %). The concentrations ranges for the four individual molecular constituents are given in Table 5. The composition of the forty samples is illustrated in FIG. 19. The training sample was prepared such that it spans wide ranges of the four analytes concentrations and encompasses as wide as possible sample composition that could be encountered in the process liquid streams. The concentration ranges of the four molecules are given in Table 5.

TABLE 5

| Concentration ranges for AcOH, DBN, APP and $H_2O$ in the prepared mixtures | | | | |
|---|---|---|---|---|
| Molecule | AcOH | DBN | APP | $H_2O$ |
| Concentration range, wt. % | 7.5-32.6 | 2.7-67.4 | 0-58.4 | 0.1-75.2 |

3.2.2. Refractometry

The reader may legitimately wonder if other, simpler inline methods could be considered instead of Raman spectroscopy. We asked ourselves similar questions while screening alternative analytical methods. Refractometry is widely applied for inline process monitoring and control, and is suitable to quantify the IL concentration in aqueous mixtures (Liu et al. 2008) (Kaneko et al. 2018). Therefore, we considered it as a serious alternative that should be investigated and conducted refractive index (RI) measurements on the set of forty samples in order to assess its potential. The RI was measured with a Peltier heated Abbe refractometer (Abbemat 300, Anton Paar, Austria) at 293.15 K.

3.2.3. Raman Spectroscopy

Samples were analyzed with an Alpha 300 R confocal Raman microscope (Witec GmbH, Germany) at ambient conditions. Nearly 100 μL of the sample were spread on a microscope concavity slide and covered with a cover glass. The Raman spectra were obtained by using a frequency doubled Nd:YAG laser (532.35 nm) at a constant power of 30 mW, and a Nikon 20× (NA=0.4) air objective. The Raman system was equipped with a DU970 N-BV EMCCD camera behind a 600 lines/mm grating. The excitation laser was polarized horizontally. After fixing the focus using the microscopy mode, each single spectrum was acquired as an average of 32 scans with an integration time of 0.5 s/scan. In total, forty spectra were collected for the forty mixtures.

3.3. Data Analysis

Data analysis and plotting were performed with Matlab® (The Mathworks, Inc.)

3.3.1. Exploratory Data Analysis: Principal Components Analysis (PCA)

The spectra were first baseline corrected using a second order polynomial and then area normalized. PCA was done on the pre-processed mean centered spectra. For more details on PCA the reader is invited to read specialized literature (Brereton 2003) (Geladi 2003) (Geladi et al. 2004).

3.3.2. Partial Least Squares Regression (PLS)

The PLS1 algorithm is used in this study to generate a model for each of the component in the sample set. The same pre-processing method as described for PCA was adopted for the PLS modelling. The decomposition into latent structures is done by maximizing the covariance between the samples preprocessed spectra and their specific analyte mean-centered concentrations using the NIPALS algorithm (Geladi and Kowalski 1986).

The model validation and selection of the adequate number of latent variables for the PLS model was done using model cross-validation procedure based on the leave-one-out method. The root-mean square error of cross validation, RMSECV, was used as quantitative measure for the selection of the model LVs. It was calculated using the following formula:

$$RMSECV = \sqrt{\frac{\sum_{i=1}^{n} (y_i - \hat{y}_i)^2}{n}}$$

where $y_i$ and $\hat{y}_i$ denote the measured and predicted values, respectively, and n the number of samples in the data set.

4. Results and Discussion 4.1. The Limitations of Refractometry

Figure 12:
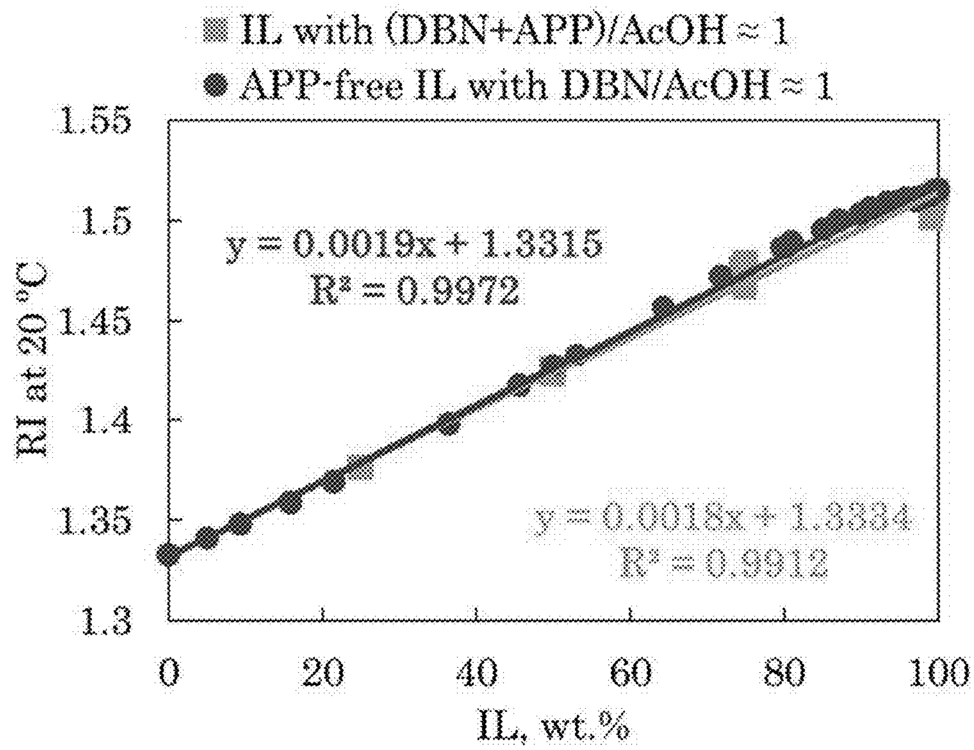
FIG. 12 illustrates comparison of RI as a function of IL wt. % in mixture with water with the presence and absence of APP according to an example.

Refractometry was first considered regarding its simplicity and the proven applicability in analyzing mixtures of ILs and water (Liu et al. 2008) (Kaneko et al. 2018). Hence, we would like to discuss our choice of further developing the Raman analytical method in the light of results we got from refractometry. The evolution of the RI for the forty samples is shown in FIG. 12. In addition to the RI measurements on the forty samples, we measured the RI for aqueous solutions of APP-free [DBNH] [OAc]/$H_2O$ mixtures, in order to assess the RI sensitivity to detect the formation of APP.

The RI evolves linearly with the IL mass fraction and the trends are very similar in the presence or absence of APP. Samples measured at similar water content but with large difference in APP content do not show any significant difference in the RI value, though some spread in the RI values can be seen at low dilution levels. Altogether, those results show that refractometry is very limited in probing the extent of DBN hydrolysis to APP and that an alternative more sensitive analytical method is needed.

FIG. 12 illustrates comparison of RI as a function of IL wt. % in mixture with water with the presence and absence of APP according to an example.

4.2. Raman Spectra of the Liquid Mixtures

Figure 13:
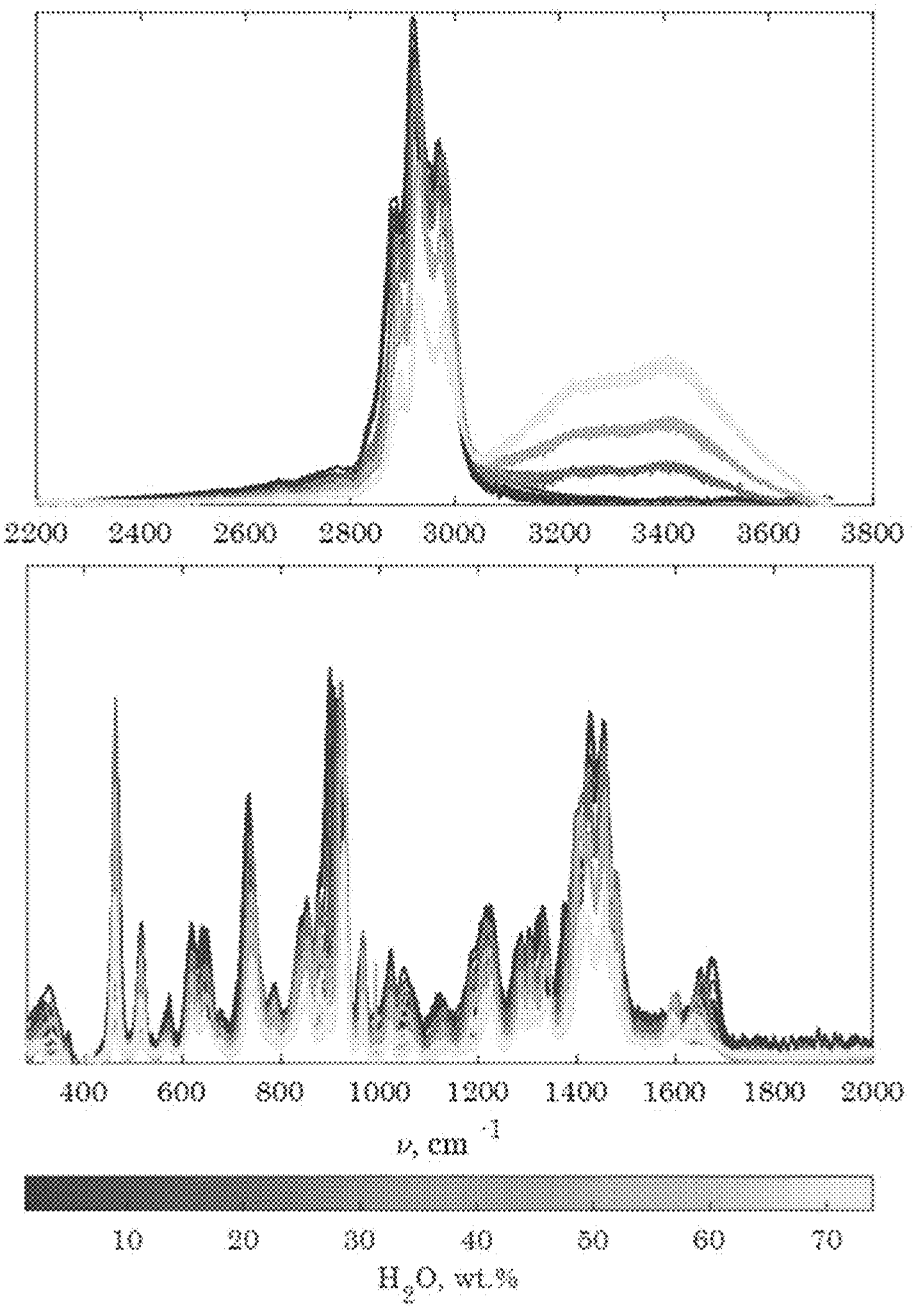
FIG. 13 illustrates pre-processed Raman spectra of the different mixtures according to an example (The color code describes the $H_2O$ wt. % in the mixture. The spectra are divided into fingerprint region (down) and high frequency region (top) for the sake of clarity.)

The pre-processed Raman spectra of the different mixtures are shown in FIG. 13. The spectra are colored according to the $H_2O$ wt. % concentration in the mixture. The samples having the same water content are clearly grouped into four distinct categories corresponding to the four dilution levels. The scatter intensity in the 3000-3700 $cm^{-1}$ region results from the OH stretching vibrations in the water molecules and increases as the water content gets higher (Sun 2009). Inversely, the scattering intensity in the 300-2000 $cm^1$ region decreases with the dilution level as it is mainly related to the other molecules. The bending mode of water (−1640 $cm^{-1}$) (Pavlovid et al. 1991) has a low influence due to its low intensity compared to the scatter intensity of the other molecules as discussed in our previous article (Guizani et al. 2020).

FIG. 13 illustrates pre-processed Raman spectra of the different mixtures according to an example (The color code describes the $H_2O$ wt. % in the mixture. The spectra are divided into fingerprint region (down) and high frequency region (top) for the sake of clarity).

Effects of $H_2O$ Addition

Figure 14:
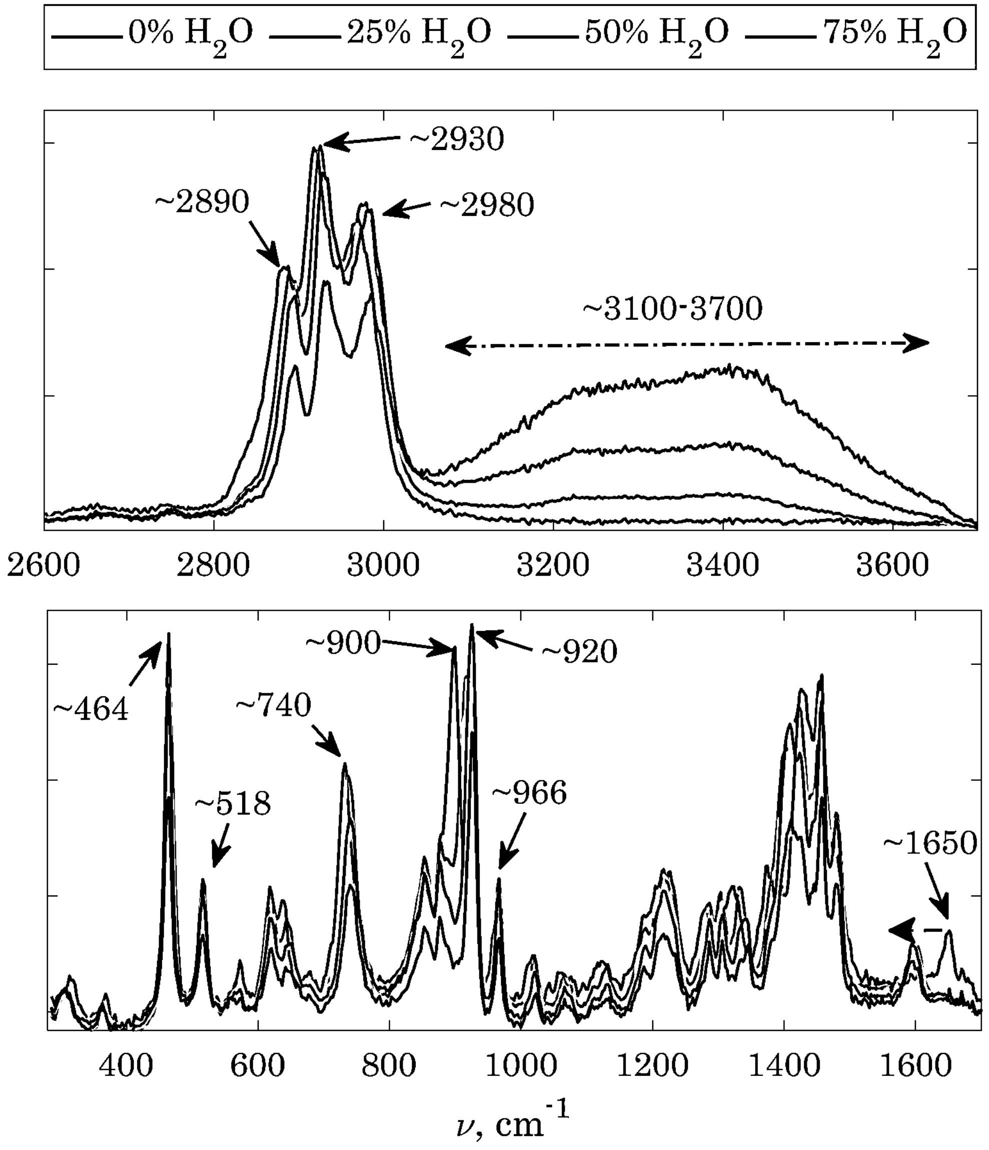
FIG. 14 illustrates pre-processed Raman spectra of four APP-free IL samples with different dilution levels according to an example (The spectra are divided into fingerprint region (down) and high frequency region (top) for the sake of clarity.)

The spectra of the four APP-free samples having different water contents are shown in FIG. 14. The band assignment was done in the light of the existing literature on the Raman spectra-structure correlations and characteristic group frequencies (Larkin 2011).

In APP-free samples, the peaks at 464 and 518 $cm^{-1}$ originate from the C—N—C bending/deformation modes in DBN. The peak around 740 $cm^{-1}$ originated most probably from the C—C vibrations in DBN. The two prominent peaks at −920 and −2930 $cm^{-1}$ were ascribed to the C—C and C—H stretching bands in AcOH, respectively. The peaks at −2890 and −2980 $cm^{-1}$ would be attributed to —$CH_2$ in phase and out of phase stretching in DBN. In the water free sample, the medium intensity band at −1650 $cm^{-1}$ was safely attributable to the C═O stretching band from AcOH.

Upon addition of water, the scattering intensity in the 280-3000 $cm^{-1}$ region decreased notably due to the dilution effect. Conversely, the broad peak related to the OH vibrations in the water molecule ~3100-3700 $cm^{-1}$ increased markedly when increasing the water content. It is well known that the Raman scattering from an analyte can show a strong dependence on the molecule's environment (Kauffmann and Fontana 2015). Thus, in addition to the intensity change due to the concentration of the analyte, band shift and shape modifications result from the change in the molecule's environment.

Interactions of the analytes with water molecules via hydrogen bonding are expected upon addition of water. Those would explain partly some modifications other than the intensity decrease in the spectra of the diluted samples. For instance, the C═O stretching band shifted down to −1600 $cm^{-1}$ which was most likely due to the structural modifications of the solutions in the presence of water (Nakabayashi et al. 1999; Gofurov et al. 2019). Further, upon addition of $H_2O$, the band at −900 $cm^{-1}$ vanished, which might indicate the absence of specific AcOH structures (dimers or trimers) that were only present in the water-free IL. At higher frequencies, the reader can notice a marked intensity decrease in the 2800-2870 $cm^{-1}$ region, reflecting modifications in the vibrational modes of DBN in the presence of water.

FIG. 14 illustrates pre-processed Raman spectra of four APP-free IL samples with different dilution levels according to an example (The spectra are divided into fingerprint region (down) and high frequency region (top) for the sake of clarity.)

Effects of APP Addition

The Raman spectra of APP-free samples and IL samples with APP/DBN=4.47 mol/mol are shown in FIG. for both cases of nearly water-free mixtures and mixtures with 75 wt. % of water. The reader can notice that there were noticeable changes in the spectra upon the variation of the APP/DBN ratio regardless of the water content. To cite a few, the bands at −464 and −516 $cm^{-1}$ decreased markedly upon the addition of APP. Those probably originated from the C—N—C bending/deformation modes in DBN which is absent in APP, even if there is still one C—N—C bond system remaining in APP. In the high-frequency region, the bands at −2890 and −2980 $cm^{1}$ attributed to —$CH_2$ in phase and out of phase stretching in DBN, decreased markedly upon the addition of APP. Upon the addition of APP, the peak around −1640-1675 $cm^{-1}$ got broader and was thought to represent the overlapped contributions from C═O in the ketone group in APP, and the C═O of the carboxylic acid group in the AcOH. A clear shift in the wavenumber range was seen when adding water to the organic mixture as discussed previously. The scattering intensity increased in the region of 332-340 $cm^{-1}$ and was assigned to the vibrational modes of δ C—C present in the aliphatic amino-propyl chain of APP.

Figure 15:
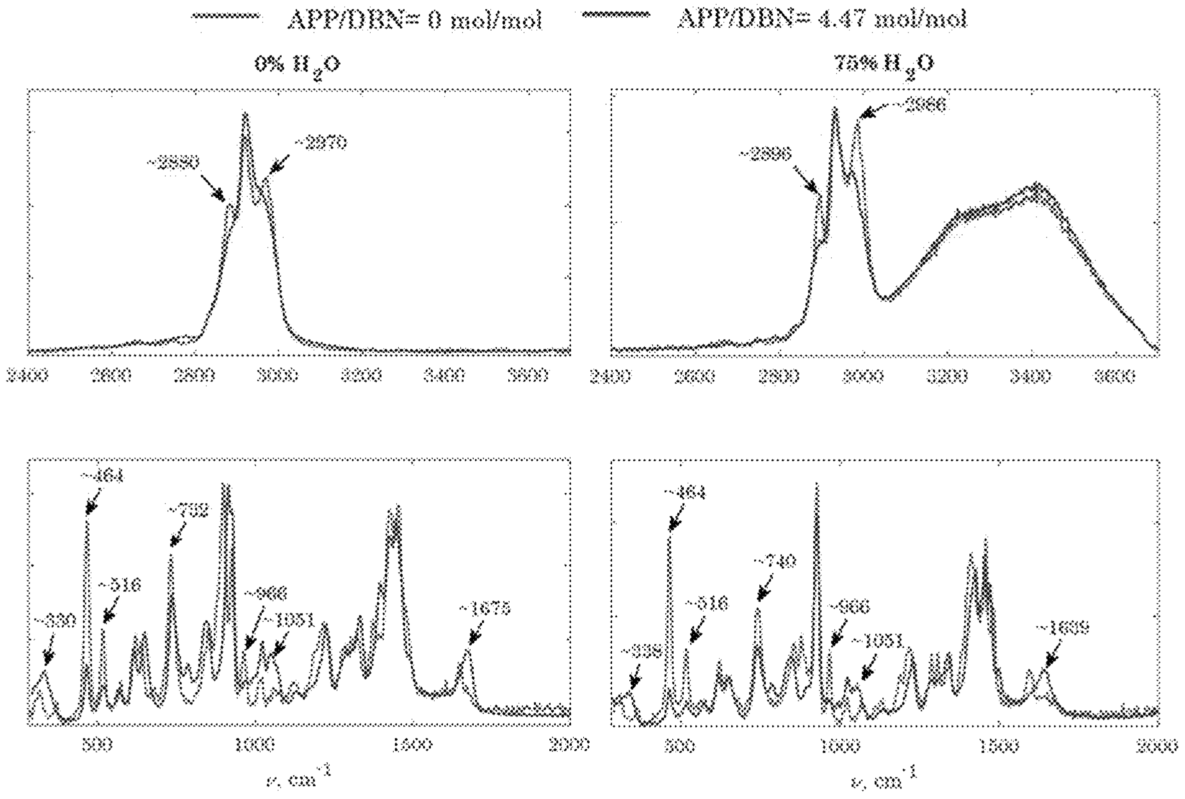
FIG. 15 illustrates pre-processed Raman spectra of an APP-free sample and a sample with APP/DBN=4.47 mol/mol, at two $H_2O$ contents of 0 wt. % (left) and 75 wt. % (right) according to an example (The spectra are divided into fingerprint region (down) and high frequency region (top) for the sake of clarity.)

FIG. 15 illustrates pre-processed Raman spectra of an APP-free sample and a sample with APP/DBN=4.47 mol/mol, at two $H_2O$ contents of 0 wt. % (left) and 75 wt. % (right) according to an example (The spectra are divided into fingerprint region (down) and high frequency region (top) for the sake of clarity).

The observed changes in the spectral features due to the variation of the APP/DBN ratio and $H_2O$ contents encouraged the development of a quantitative analysis using the Raman spectra.

4.3. Principal Component Analysis (PCA)

PCA is a method for data reduction and visualization. It is in the core of chemometrics and is commonly used for an exploratory multivariate data analysis and unsupervised pattern recognition. In PCA, the dimensionality of the data set is reduced by transforming the original spectral data set into a smaller data set composed by few uncorrelated variables (PCs), which retain most of the variation present in all the original variables. The aim is to identify the direction of greatest variability in the data and interpret them in terms of the underlying chemistry.

Figure 22:
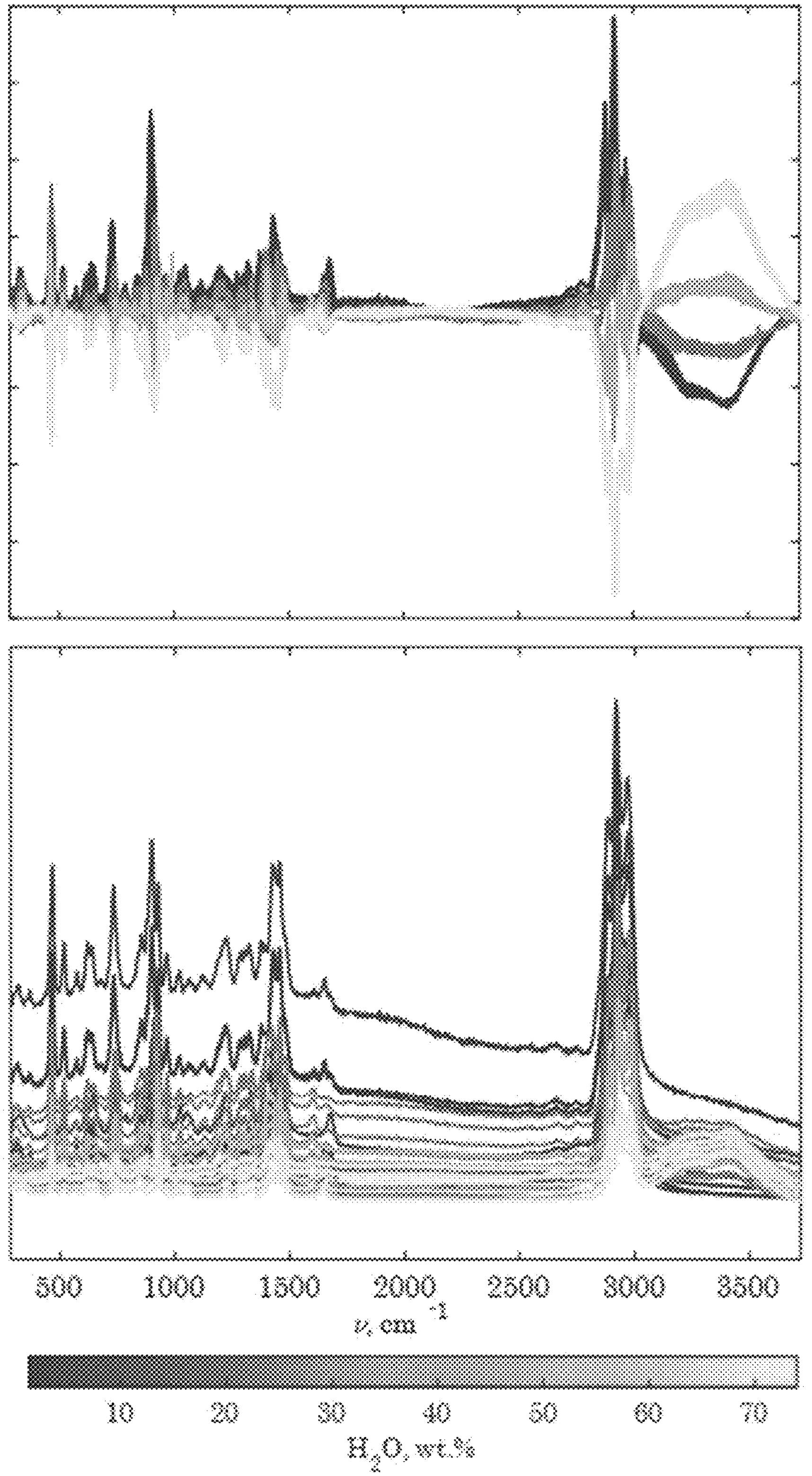
FIG. 22 illustrates raw (top) and mean-centered pre-processed Raman spectra of the different samples according to an example (The color code is indicative of the $H_2O$ wt. % in the mixtures.)

PCA was performed on the pre-processed (background corrected, area normalized and meancentered) data (see FIG. 22 for a comparison between the original and the pre-processed, mean-centered spectra). The results show that more than 99% of the variance in the data was captured by the first three PCs (see FIG. 23). The first PC explained 89% of the variance, while the three following ones explained respectively 5.1%, 4.4% and 0.52%. The pseudo-rank of the data matrix should be therefore three or four, which was physically reasonable since four different molecules were present in the mixtures and contributing to the scattering. The sample $N^{35}$ showed difficulties during the pre-processing (background subtraction) and had very high Hoteling $T^2$ and Q residual values. It was consequently considered as an outlier and excluded from the decomposition procedure.

Figure 16:
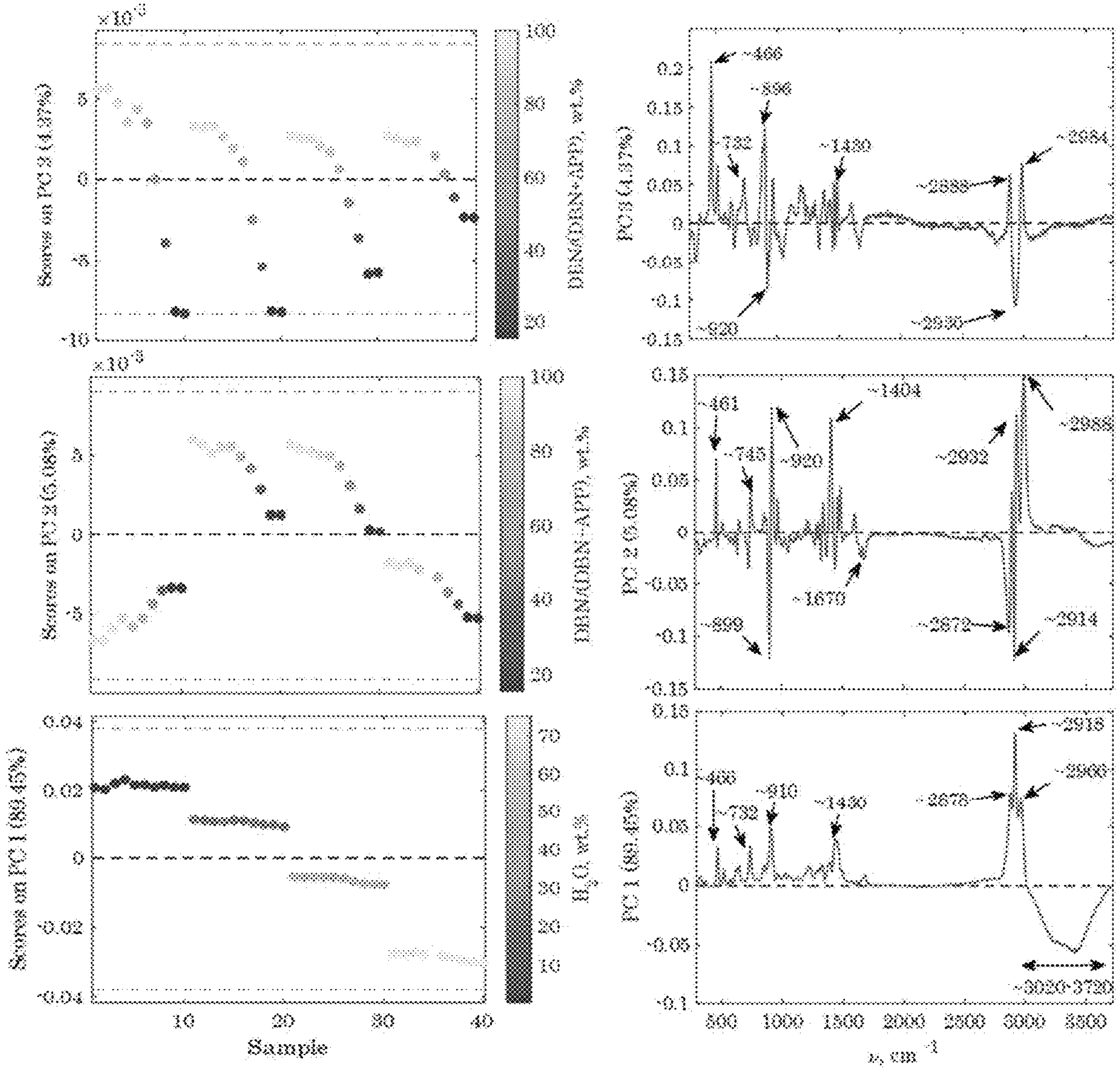
FIG. 16 illustrates scores (left) and loadings plots for the three first PCs according to an example.

The scores and loadings of the first three PCs are shown in FIG. 16. For PC1, the scores were colored according to the $H_2O$ wt. % in the mixtures. PC1 scores were related to the water content in the different mixtures. Samples having the same water content had similar scores on PC1, which showed positive contributions in the ~280-1800 $cm^{-1}$ region (corresponding mainly to the scattering from DBN, APP and AcOH), and negative ones in the ~3020-3720 $cm^{-1}$ region (corresponding mainly to the scattering from $H_2O$).

Figure 20:
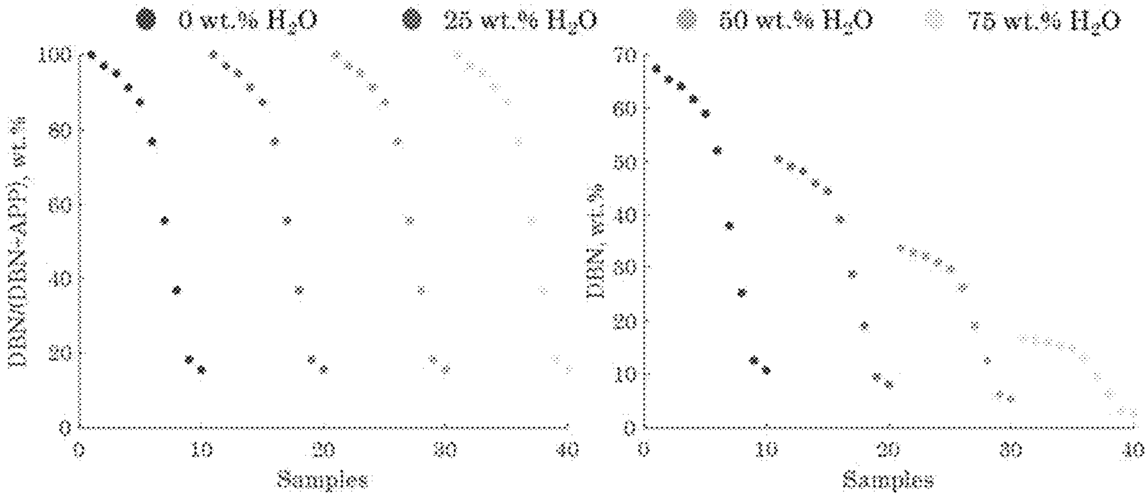
FIG. 20 illustrates ratio of DBN to DBN+APP (left) and DBN wt. % in the mixtures (right) according to an example.

PC2 and PC3 separated the samples within each group according to the proportion of DBN in the sum of DBN and APP. PC2 and PC3 indicated also some interesting features. In PC2, the water-free samples and the samples with the highest water content had negative scores and are separated from the less extreme samples having respectively 25 wt. % and 50 wt. % $H_2O$ and positive scores. In PC3, the spread in scores became narrower as the dilution increased, and the shape of the scores for the different samples was very similar to the shape of DBN wt. % in the mixture as shown in FIG. 20. Altogether, the PCA decomposition showed that the variance in the data could be captured almost entirely in the four first components. These four PCs reflected most of the chemical information according to the different sample compositions.

FIG. 16 illustrates scores (left) and loadings plots for the three first PCs according to an example.

4.4. Partial Least Squares Regression (PLS) for the Quantification of DBN, APP, AcOH and $H_2O$ in the Liquid Mixtures 4.4.1. PLS Model Based on the Entire Spectra The PLS model was built on thirty-nine samples after discarding sample N35, which showed some signal anomalies and for which the background correction was unsuccessful resulting in a high Q residual and a clear outlier behavior when included in the models. The results from the PLS regression are shown in Table 6. As the PLS1 algorithm was adopted for the regression, each component was modeled separately. This choice was motivated by the fact that PLS1 regression results in a lower error than PLS2 with which all components are modeled simultaneously (Brereton 2003).

The number of chosen LVs varied between 3 and 5 for the different models. Each of the models captured more than 96% of the variability in the predictor (spectra) and more than 99% of the variability in the response (concentrations).

TABLE 6

PLS regression results: explained variances and RMSECVs

| Component | LVs | X var % | Y var % | RMSEC, wt. % | RMSECV, wt. % | $R^2$ | Range, wt. % |
|---|---|---|---|---|---|---|---|
| AcOH | 3 | 98.7 | 99.9 | 0.20 | 0.23 | 0.999 | 7.5-32.6 |
| DBN | 4 | 99.1 | 99.7 | 1.73 | 2.09 | 0.992 | 2.7-67.4 |
| APP | 5 | 99.6 | 99.8 | 0.81 | 1.15 | 0.998 | 0-58.4 |
| $H_2O$ | 3 | 96.9 | 99.9 | 0.68 | 0.64 | 0.999 | 0.1-75.2 |

Figure 17:
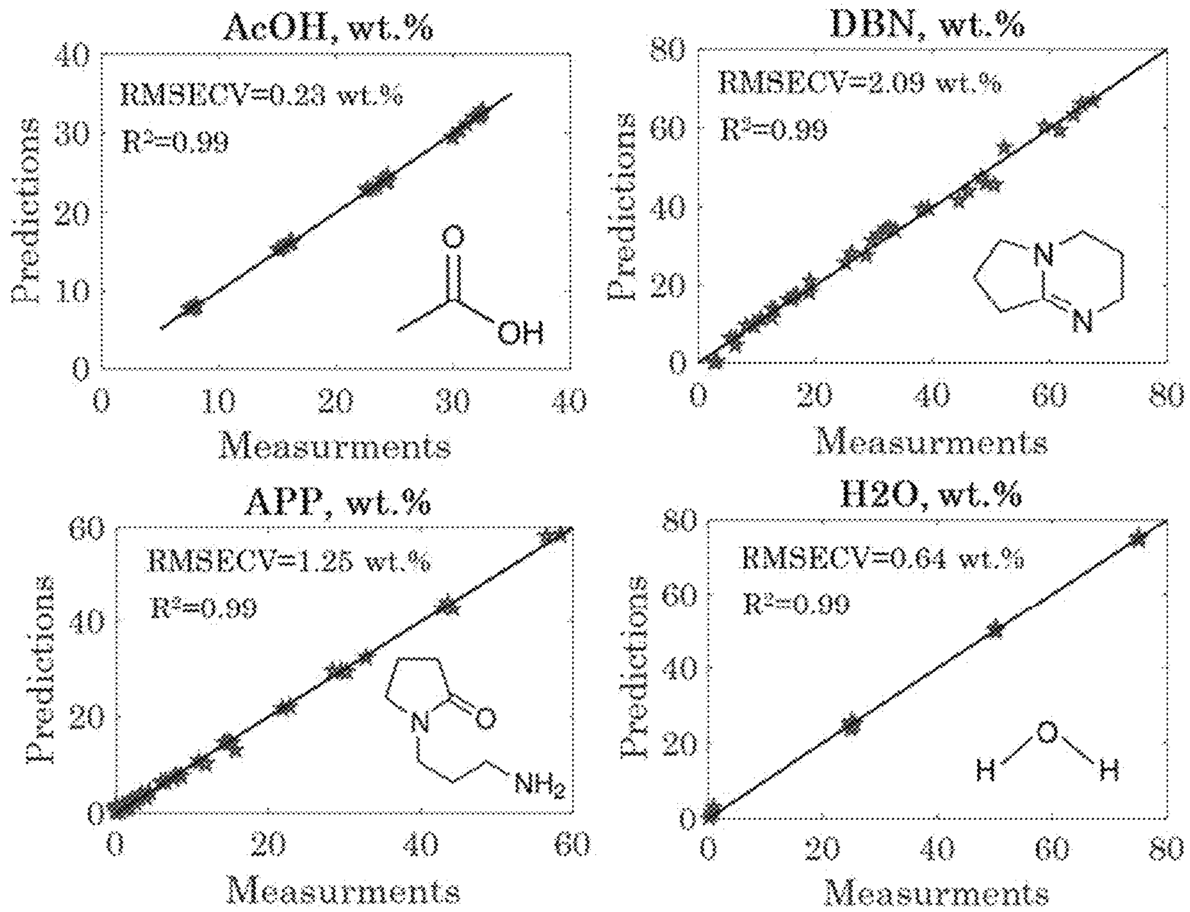
FIG. 17 illustrates cross-validation predicted vs measured concentrations of AcOH, DBN, APP and $H_2O$ according to an example.

The RMSECV for the AcOH, DBN, APP and $H_2O$ were 0.23 wt. %, 2.09 wt. %, 1.15 wt. % and 0.64 wt. %, respectively. The model showed a better predictability for AcOH and $H_2O$ than for DBN and APP, although the results were still in a good range for the two last molecules. FIG. 17 shows the cross-validation predicted versus measured concentrations of AcOH, DBN, APP and $H_2O$. The reader can notice that the data points for the four molecules lie very close to the 1:1 identity line. The Pearson correlation coefficient was above 0.99 for the four cases. Overall, the analytical method showed very good results even for more complex mixtures containing APP. Additional data about the PLS models are given in the ESI. It is important finally to stress the universality of such analytical methods based on spectroscopy and multivariate analysis. The applications are practically unlimited, and readers are encouraged to try applying them on their own systems where variations in signal intensities could be correlated to the analyte concentration.

FIG. 17 illustrates cross-validation predicted vs measured concentrations of AcOH, DBN, APP and $H_2O$ according to an example.

4.4.2. Enhancing the PLS Model Prediction Performance Through Variable Selection The purpose of variable selection is to obtain a model that is easier to understand, and which has better predictive performances. In searching for the best variable selection procedure, one might be tempted to try all possible combinations of the predictor variables in order to select the best one. However, this turns out to be prohibitive due to the large number of variables and causes a high risk of overfitting when the number of variables is higher than the number of samples (Andersen and Bro 2010). Both, conditions are encountered when dealing with spectroscopic data. Therefore, the purpose here is not to search for the best model, but for a better one, in terms of prediction and understanding.

Figure 18:
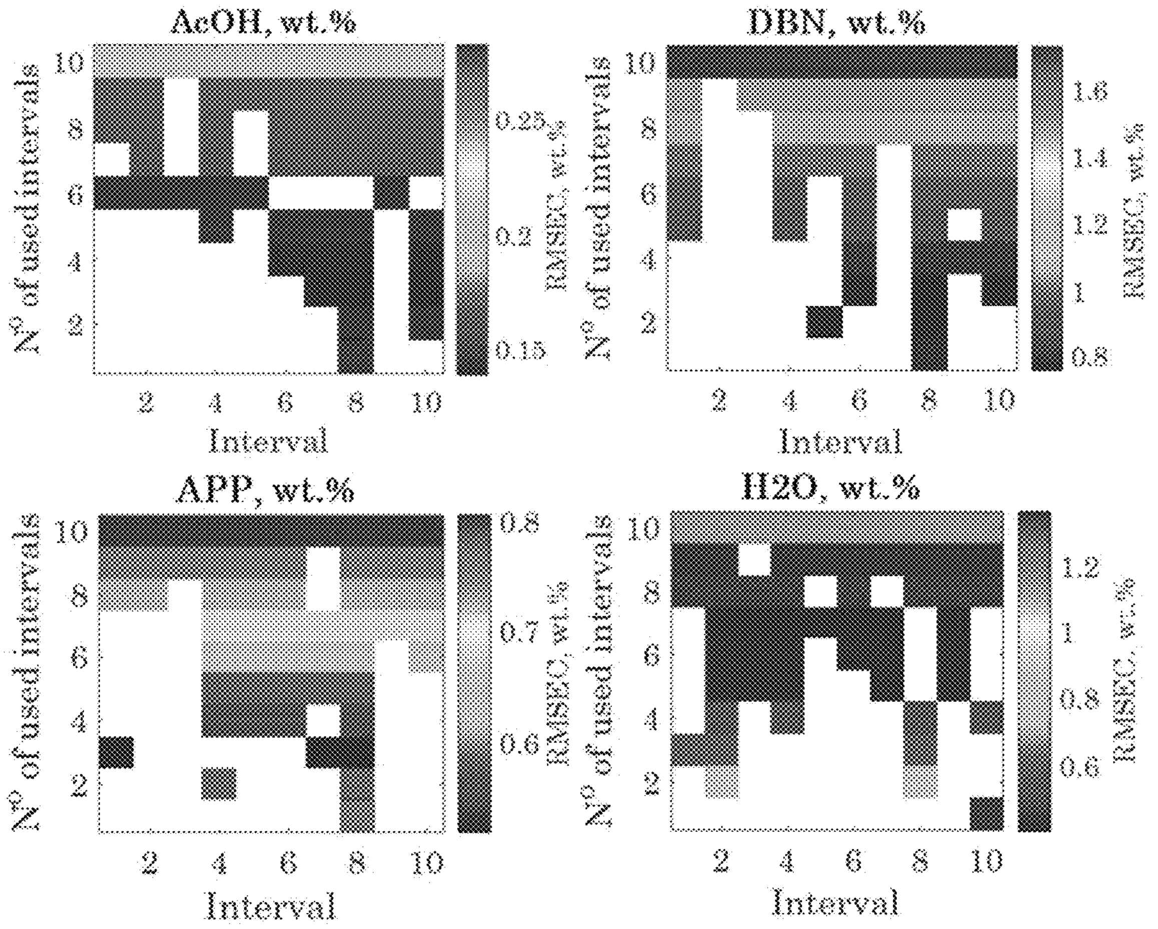
FIG. 18 illustrates lowest RMSEC values for the 10 best models using an increasing number of intervals according to an example.

With this regard, we adopted a simple method in which the spectral range was divided into 10 subintervals and PLS models were determined based on all possible interval combinations. The algorithm calculated the RMSEC for all combinations and chose the combination that resulted in the lowest RMSEC. The results are shown in FIG. 18. The reader can see for instance that taking the whole spectrum to predict DBN or APP results in the worst prediction case in terms of lowest possible RMSEC. For AcOH and $H_2O$, the worst case in terms of lowest RMSEC is obtained with one subinterval.

FIG. 18 illustrates lowest RMSEC values for the 10 best models using an increasing number of intervals according to an example.

The best cases for lowest RMSEC were found between those two extremes. They are summarized in Table 7 with the optimal number of subintervals and the corresponding lowest RMSEC. The reader can notice that with this simple procedure, the model calibration errors can be further reduced.

TABLE 7

PLS regression results: explained variances and RMSECVs

| Component | RMSEC before iPLS, wt. % | RMSEC after iPLS, wt. % | No. of intervals for minimum RMSEC |
|---|---|---|---|
| AcOH | 0.20 | 0.14 | 3 |
| DBN | 1.73 | 0.76 | 2 |
| APP | 0.81 | 0.52 | 3 |
| $H_2O$ | 0.68 | 0.41 | 7 |

FURTHER EXAMPLES

A. Sample Preparation

TABLE 8

Specifications of the original [APPH][OAc] and [DBNH][OAc] stock solutions

| Weight fractions | [APPH][OAc] stock solution | [DBNH][OAc] stock solution |
|---|---|---|
| $H_2O$ (KFT), wt. % | 0.97% | 0.05% |
| APP+, wt. % of dry | 63.0% | 0.0% |
| DBN+, wt. % of dry | 12.1% | 75.4% |
| HOAc, wt. % of dry | 24.9% | 24.6% |
| [APPH][OAc], wt. % of dry | 83.9% | 0.0% |
| [DBNH][OAc], wt. % of dry | 16.1% | 100% |

FIG. 19 illustrates sample composition according to an example.

B. Raman Spectroscopy Analysis

FIG. 20 illustrates ratio of DBN to DBN+APP (left) and DBN wt. % in the mixtures (right) according to an example.

Figure 21:
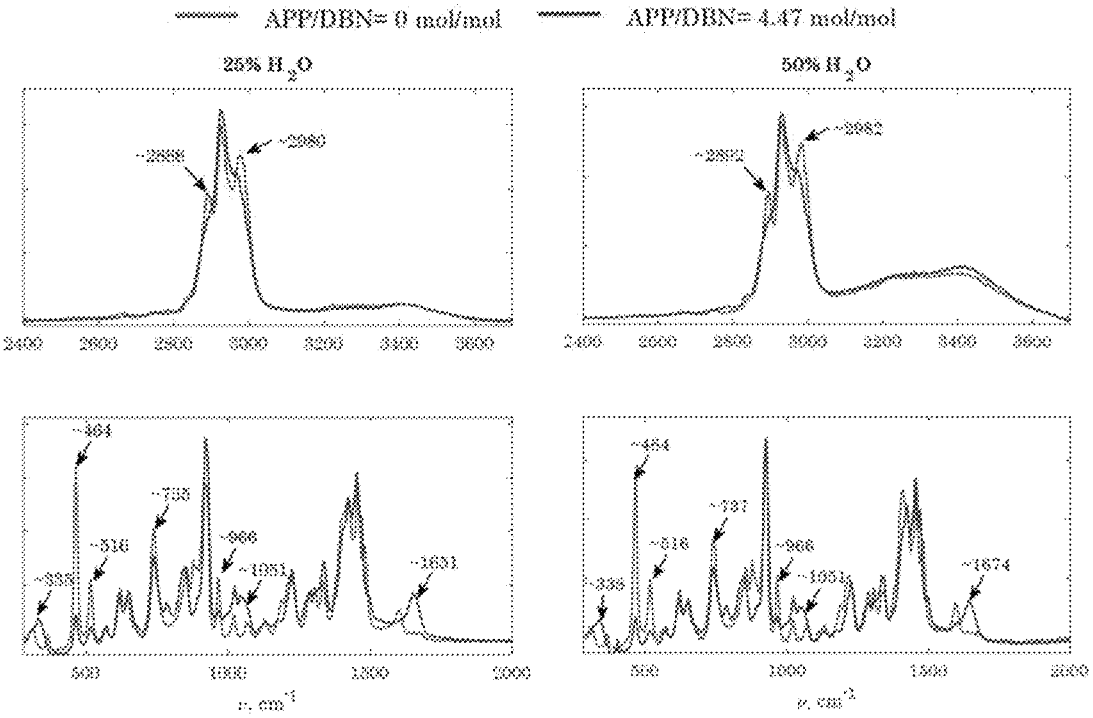
FIG. 21 illustrates pre-processed Raman spectra of the samples having APP/DBN mol ratios of 0 and 4.47, at two $H_2O$ contents of 25 wt. % (left) and 50 wt. % (right) according to an example (The spectra are divided into fingerprint region (down) and high frequency region (top) for the sake of clarity)

FIG. 21 illustrates pre-processed Raman spectra of the samples having APP/DBN mol ratios of 0 and 4.47, at two $H_2O$ contents of 25 wt. % (left) and 50 wt. % (right) according to an example (The spectra are divided into fingerprint region (down) and high frequency region (top) for the sake of clarity).

C. PCA

FIG. 22 illustrates raw (top) and mean-centered preprocessed Raman spectra of the different samples according to an example (The color code is indicative of the $H_2O$ wt. % in the mixtures).

Figure 23:
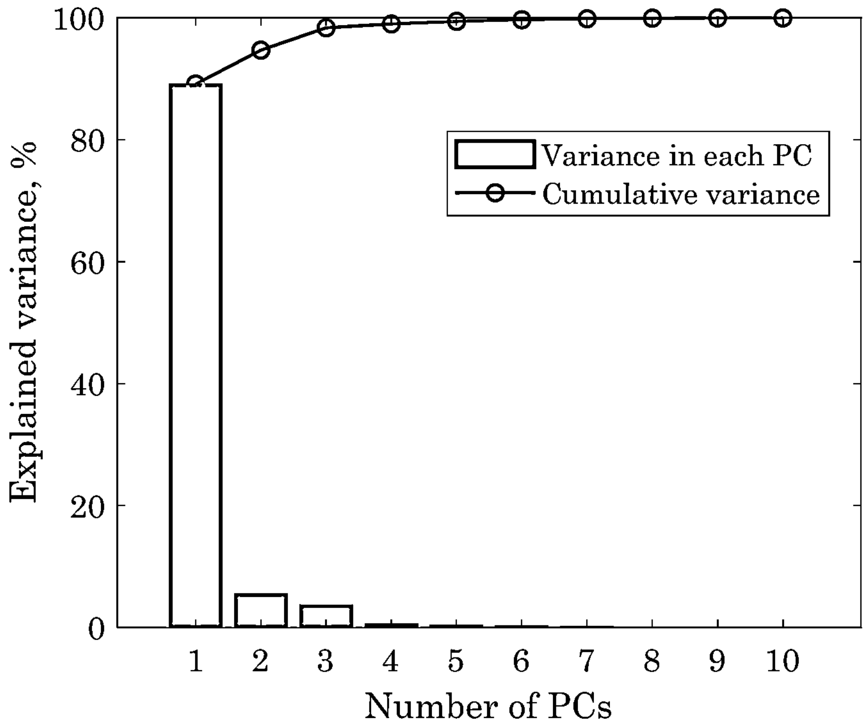
FIG. 23 illustrates variance and cumulative variance explained by the ten first PCs according to an example.

FIG. 23 illustrates variance and cumulative variance explained by the ten first PCs according to an example.

D. PLS Models a. AcOH

Figure 24:
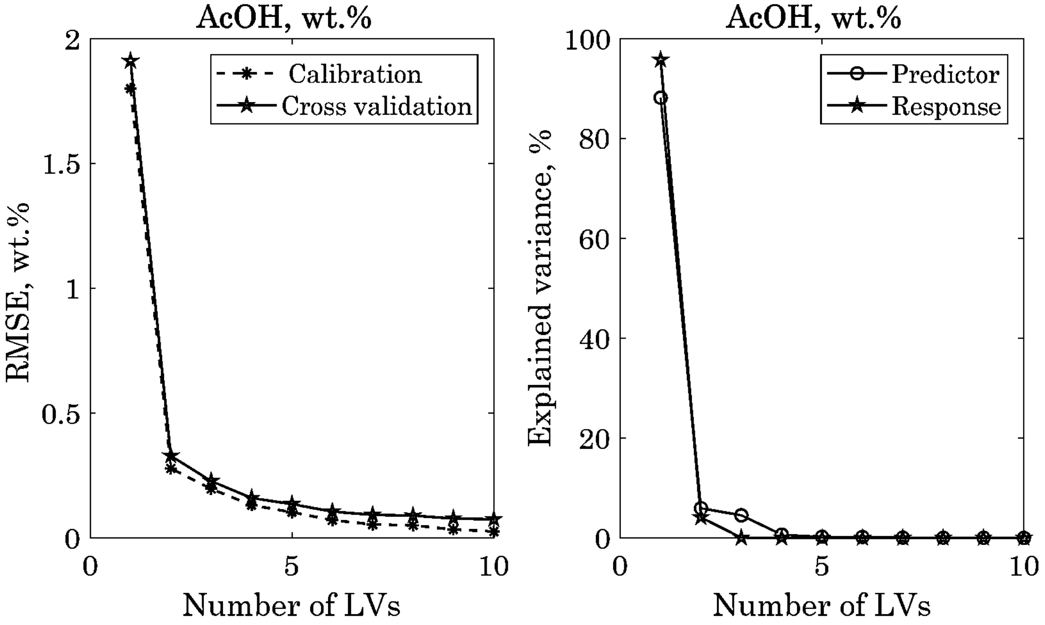
FIG. 24 illustrates RMSEs and Variances as a function of the number of LVs according to an example.

FIG. 24 illustrates RMSEs and Variances as a function of the number of LVs according to an example.

Figure 25:
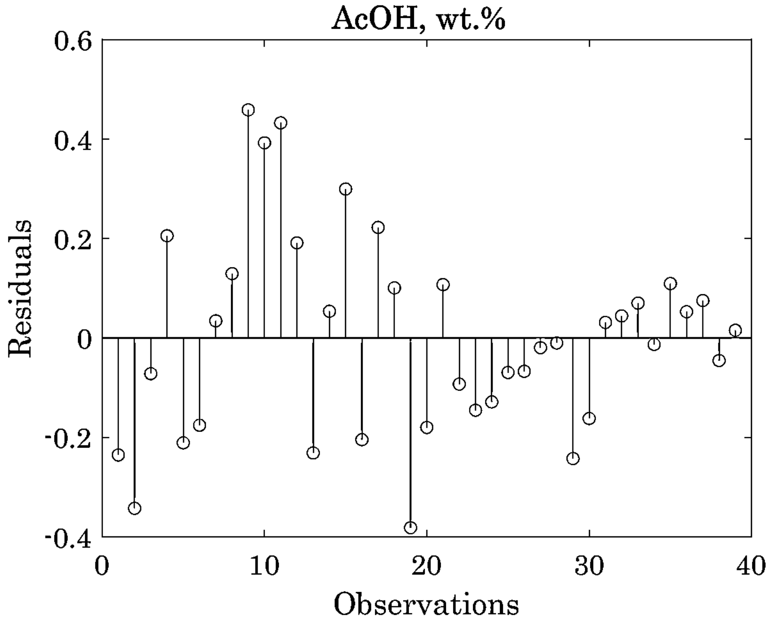
FIG. 25 illustrates model residuals according to an example.

FIG. 25 illustrates model residuals according to an example.

Figure 26:
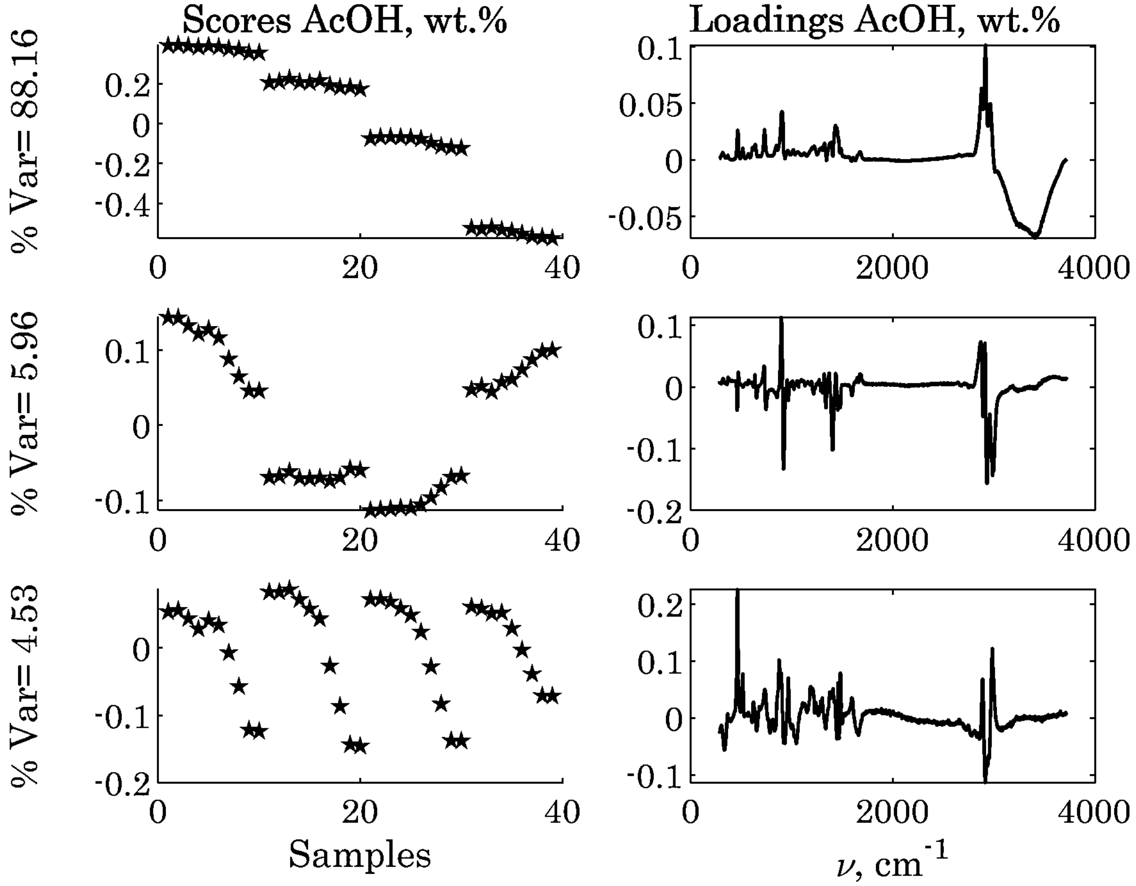
FIG. 26 illustrates model scores and loadings according to an example.

FIG. 26 illustrates model scores and loadings according to an example.

Figure 27:
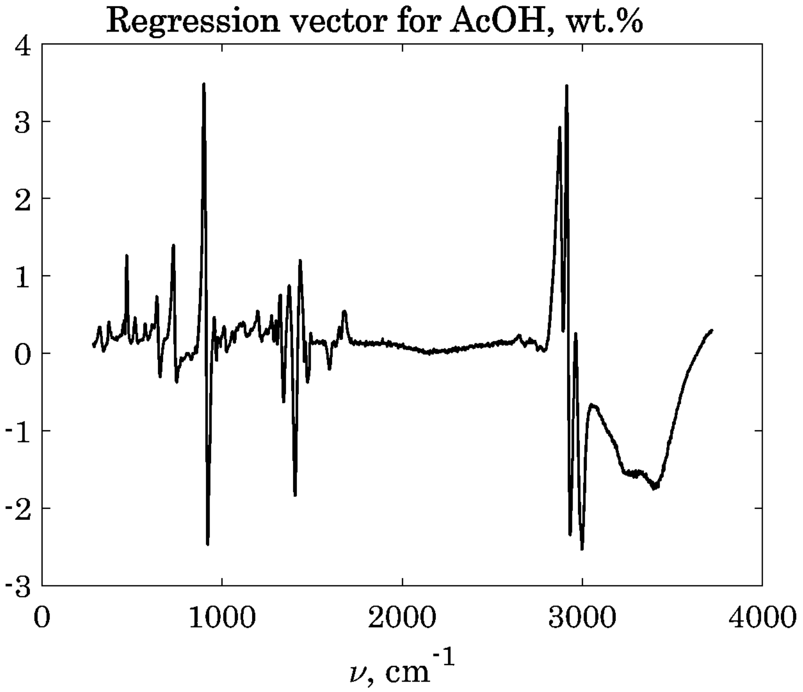
FIG. 27 illustrates model regression vector according to an example.

FIG. 27 illustrates model regression vector according to an example.

b. DBN

Figure 28:
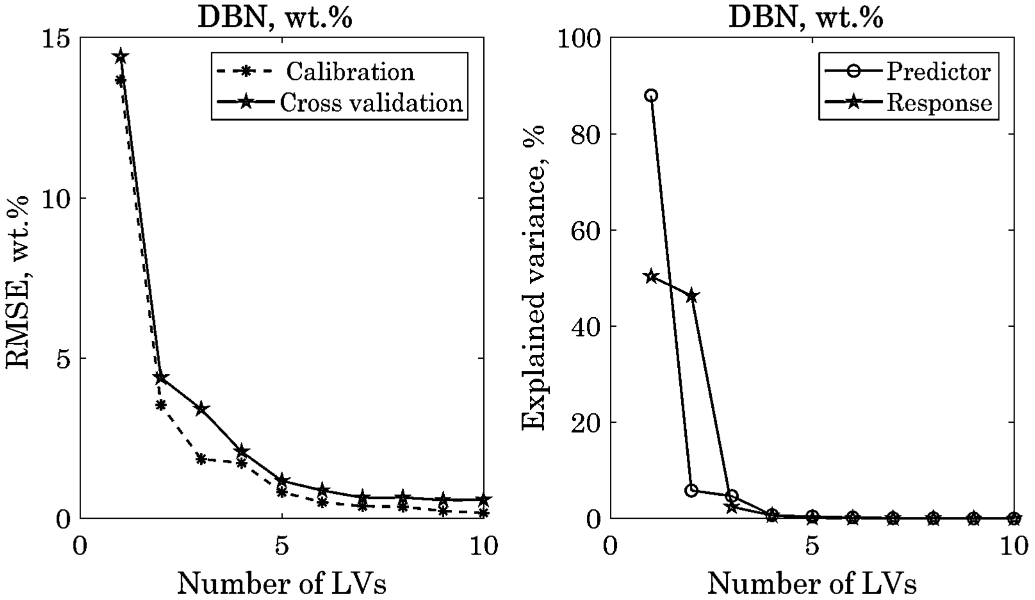
FIG. 28 illustrates RMSEs and Variances as a function of the number of LVs according to an example.

FIG. 28 illustrates RMSEs and Variances as a function of the number of LVs according to an example.

Figure 29:
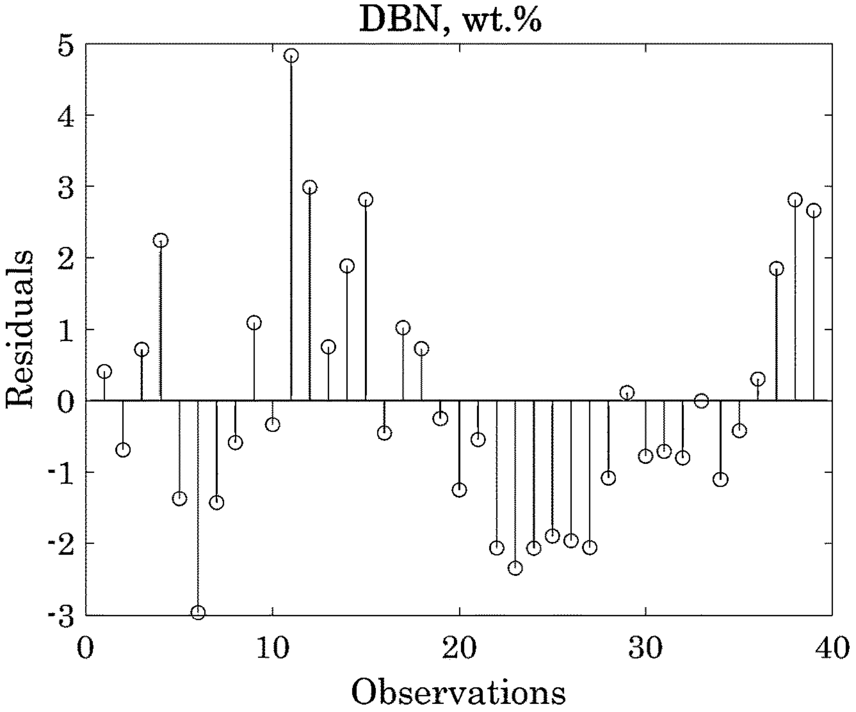
FIG. 29 illustrates model residuals according to an example.

FIG. 29 illustrates model residuals according to an example.

Figure 30:
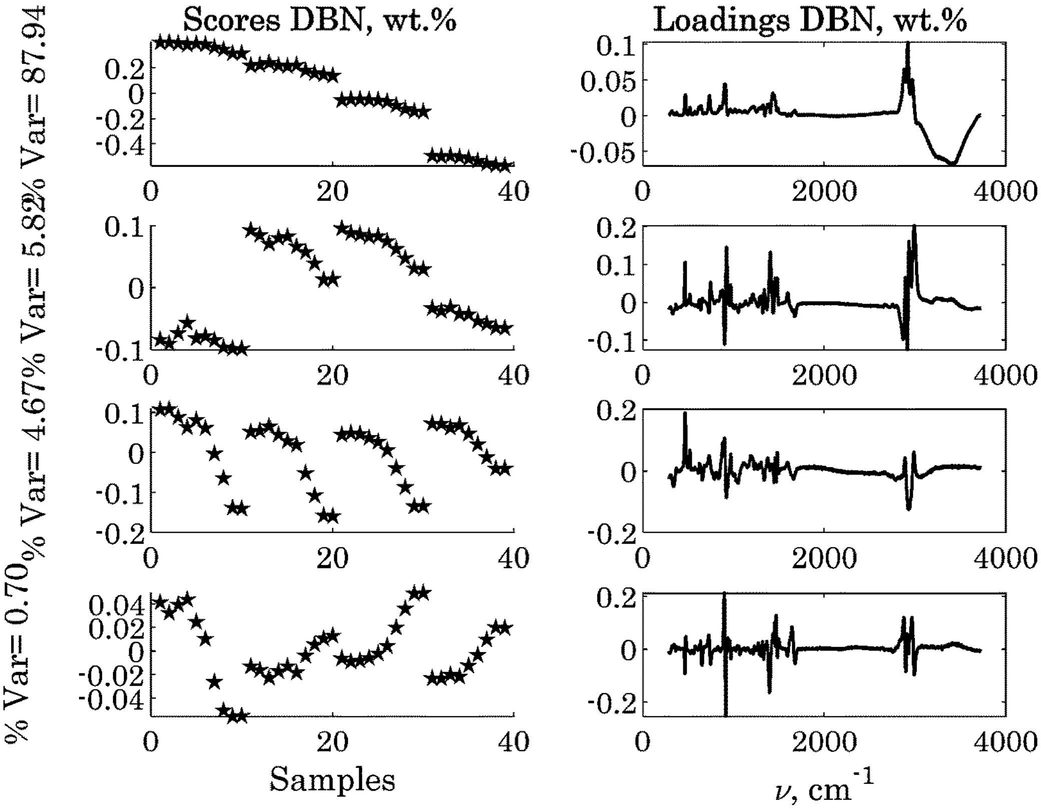
FIG. 30 illustrates model scores and loadings according to an example.

FIG. 30 illustrates model scores and loadings according to an example.

Figure 31:
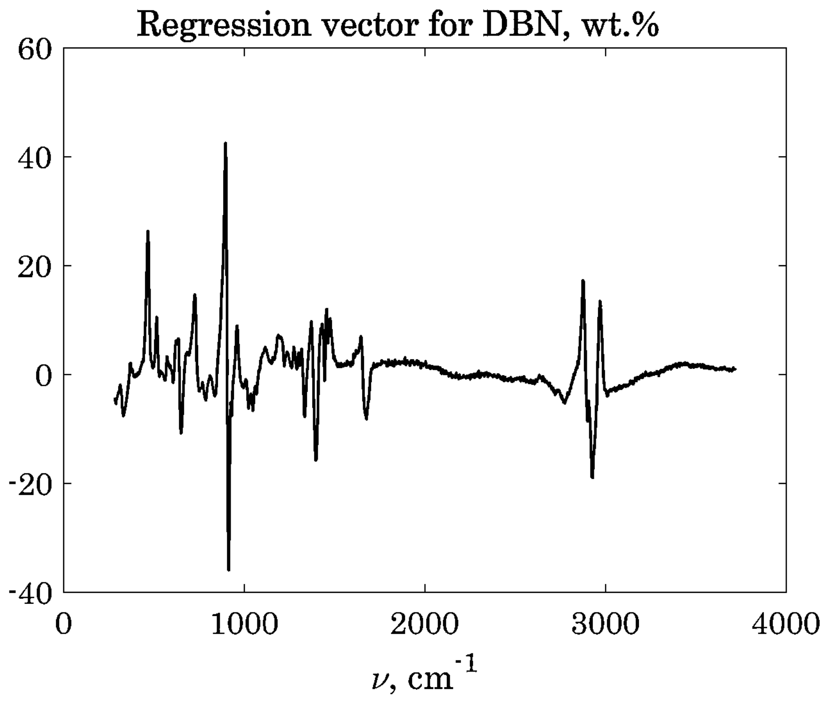
FIG. 31 illustrates model regression vector according to an example.

FIG. 31 illustrates model regression vector according to an example.

c. APP

Figure 32:
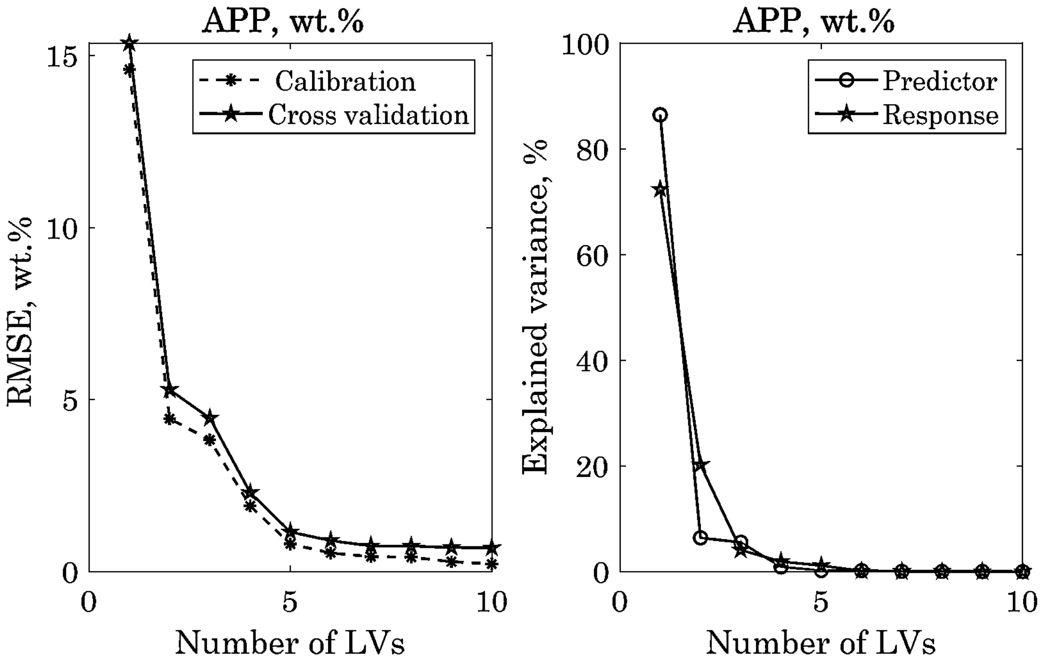
FIG. 32 illustrates RMSEs and Variances as a function of the number of LVs according to an example.

FIG. 32 illustrates RMSEs and Variances as a function of the number of LVs according to an example.

Figure 33:
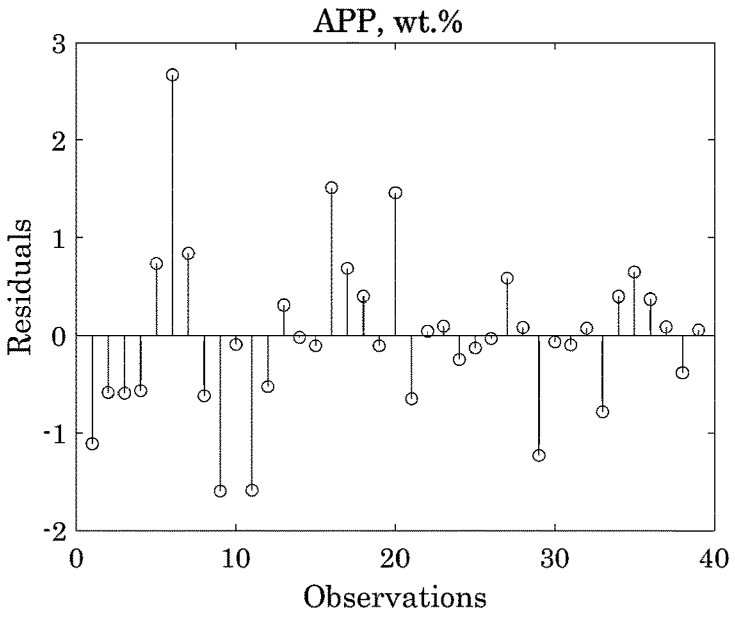
FIG. 33 illustrates model residuals according to an example.

FIG. 33 illustrates model residuals according to an example.

Figure 34:
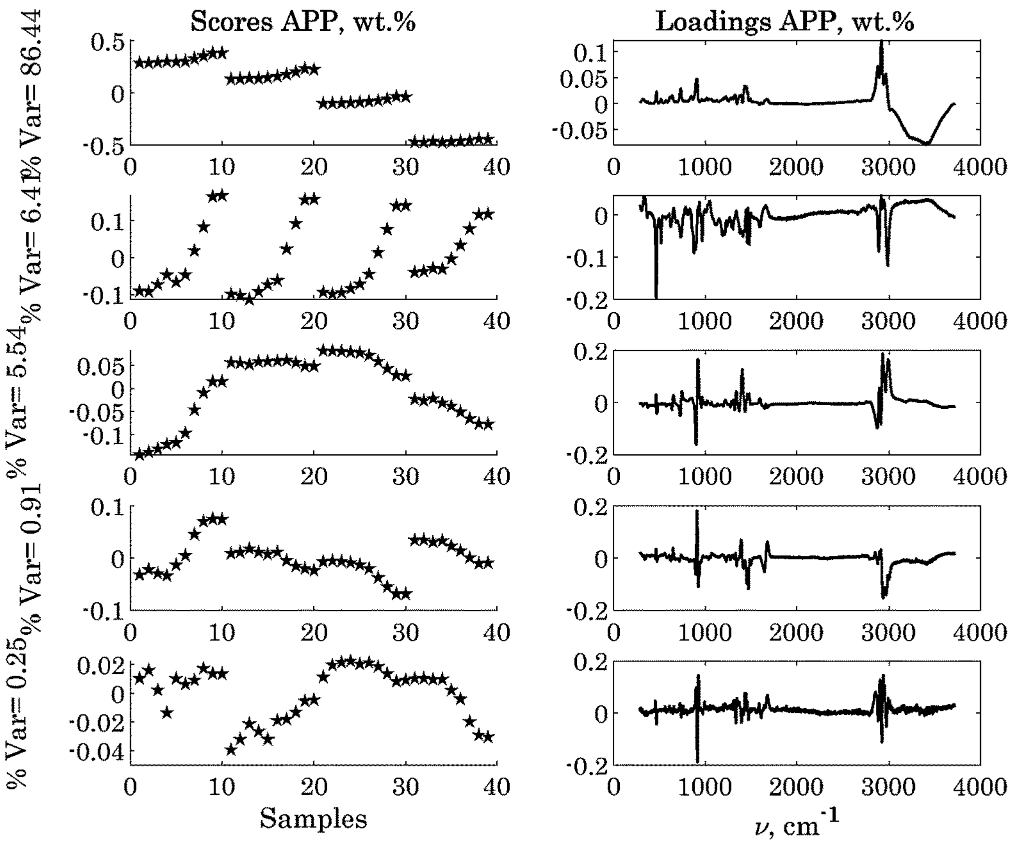
FIG. 34 illustrates model scores and loadings according to an example.

FIG. 34 illustrates model scores and loadings according to an example.

Figure 35:
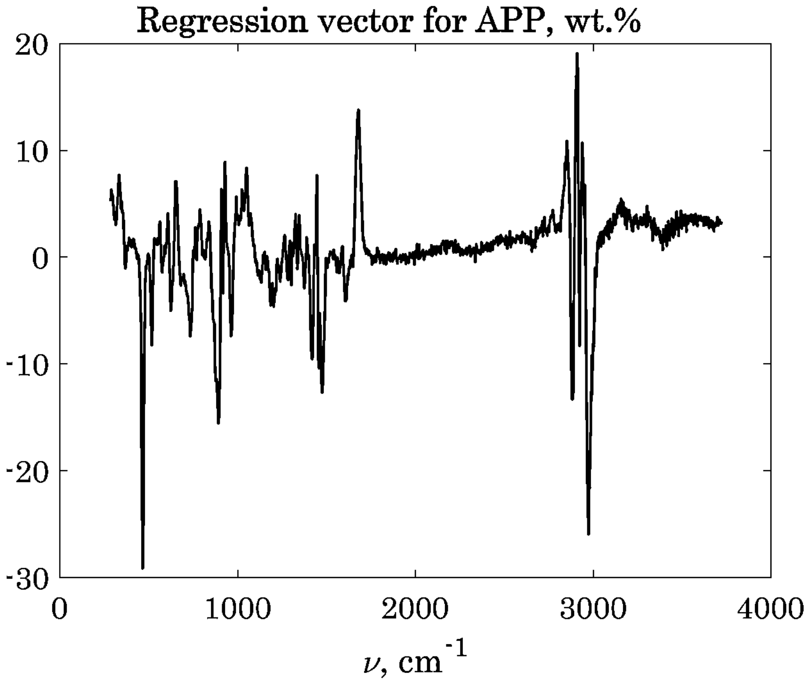
FIG. 35 illustrates model regression vector according to an example.

FIG. 35 illustrates model regression vector according to an example.

d. $H_2O$

Figure 36:
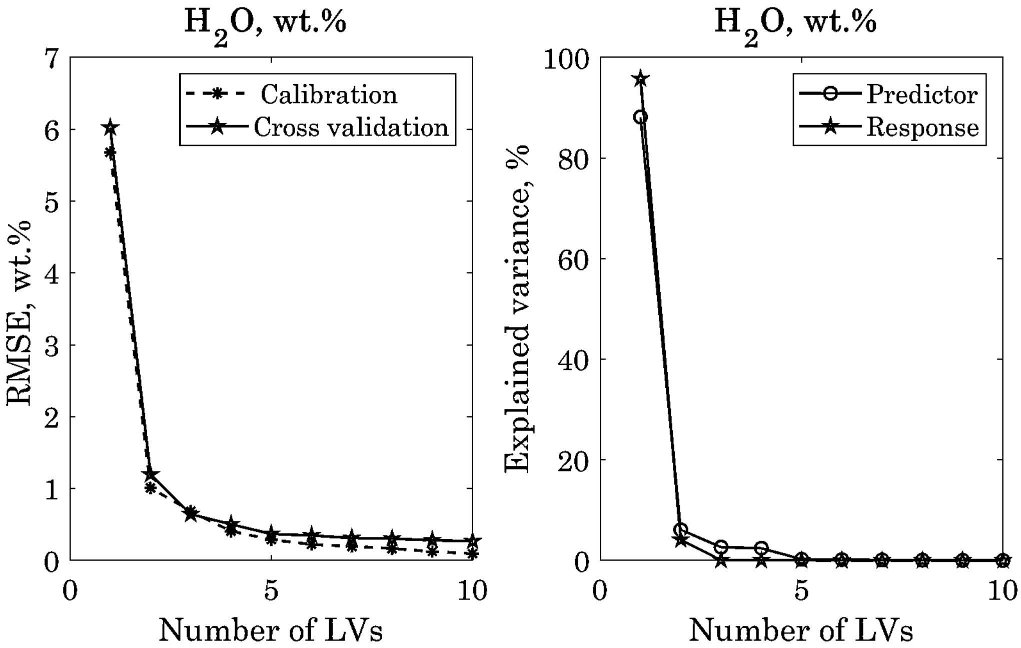
FIG. 36 illustrates RMSEs and Variances as a function of the number of LVs according to an example.

FIG. 36 illustrates RMSEs and Variances as a function of the number of LVs according to an example.

Figure 37:
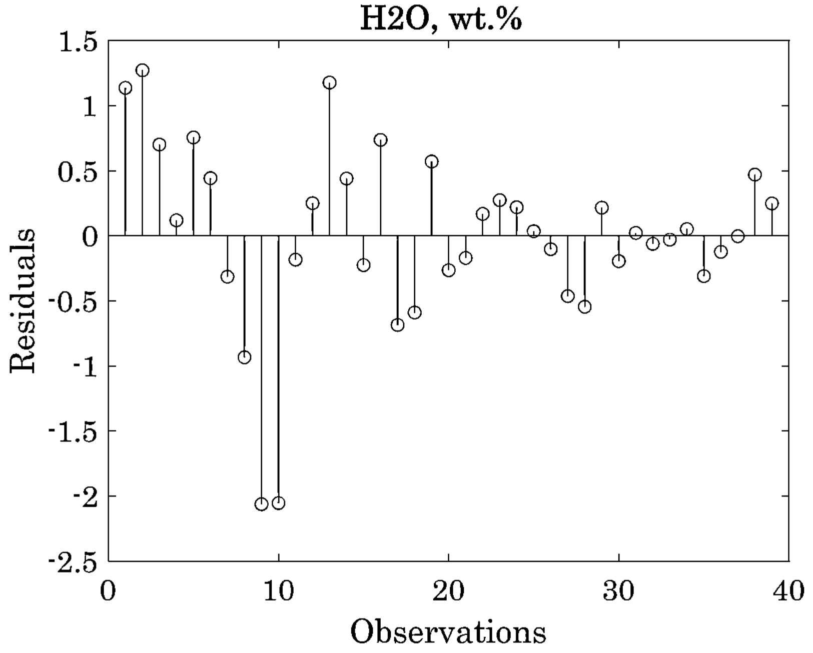
FIG. 37 illustrates model residuals according to an example.

FIG. 37 illustrates model residuals according to an example.

Figure 38:
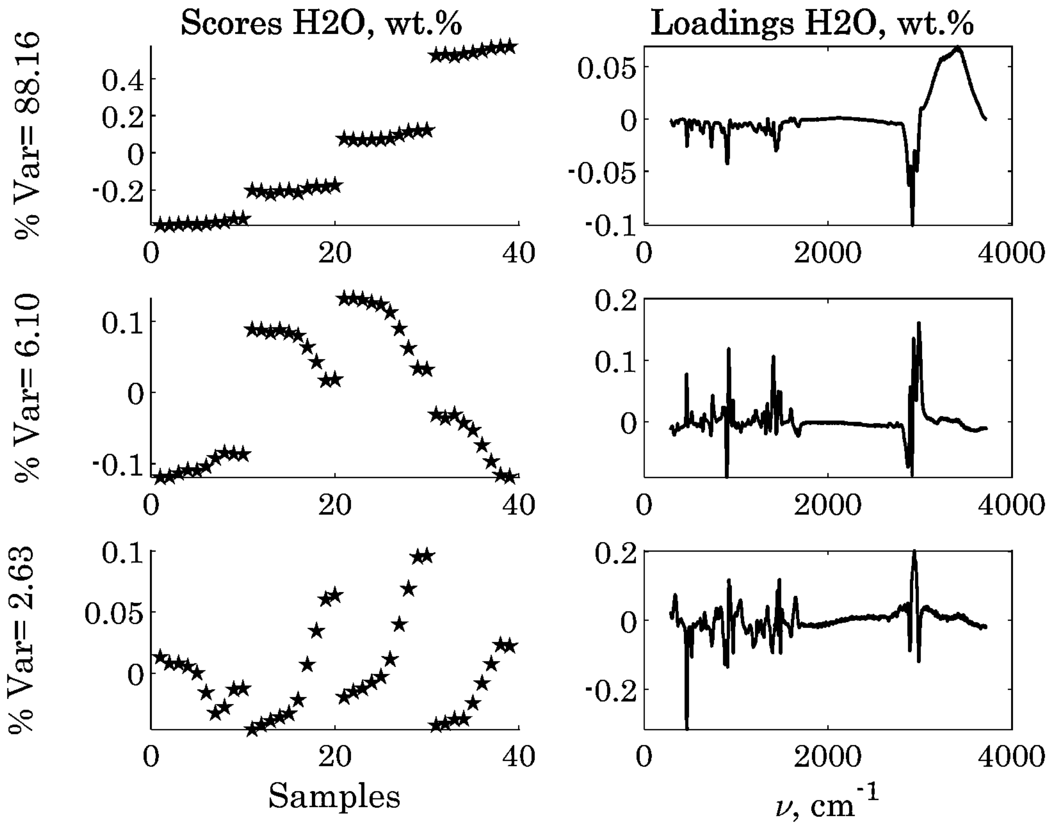
FIG. 38 illustrates model scores and loadings according to an example and FIG. 39 illustrates model regression vector according to an example.

FIG. 38 illustrates model scores and loadings according to an example.

Figure 39:
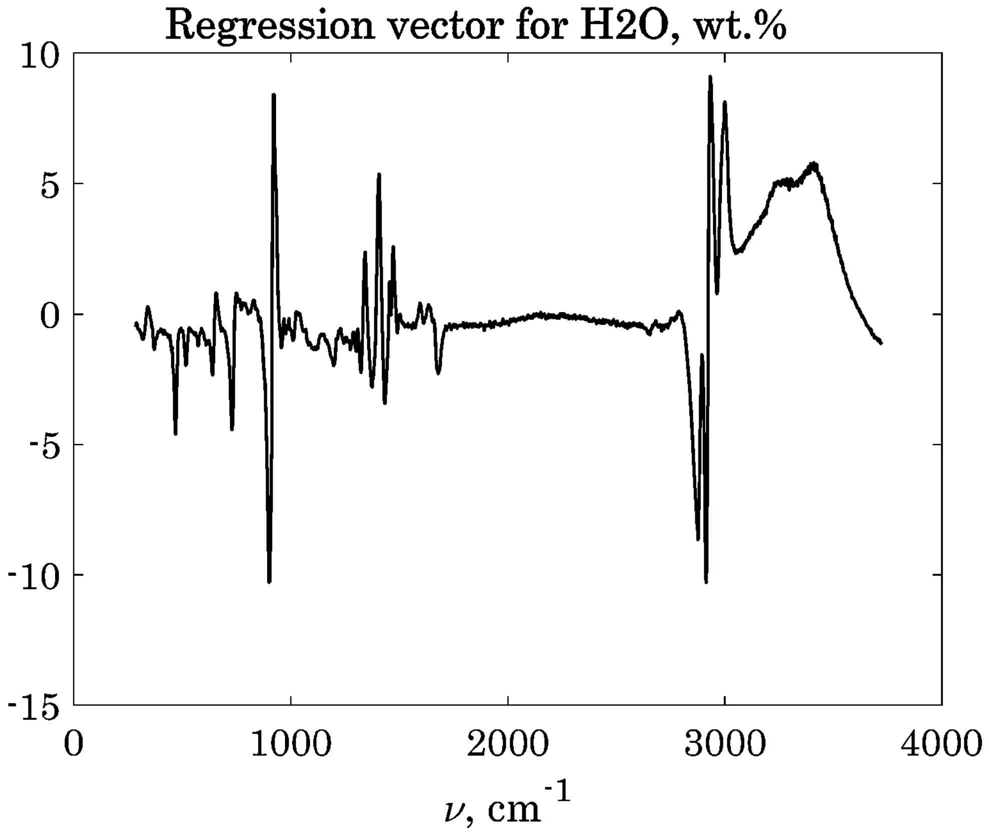

FIG. 39 illustrates model regression vector according to an example.

The different functions discussed herein may be performed in a different order and/or concurrently with each other.

Any range or device value given herein may be extended or altered without losing the effect sought, unless indicated otherwise. Also, any example may be combined with another example unless explicitly disallowed.

Although the subject matter has been de-scribed in language specific to structural features and/or acts, it is to be understood that the subject matter defined in the appended claims is not necessarily limited to the specific features or acts de-scribed above. Rather, the specific features and acts described above are disclosed as examples of implementing the claims and other equivalent features and acts are intended to be within the scope of the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item may refer to one or more of those items.

The term 'comprising' is used herein to mean including the method, blocks or elements identified, but that such blocks or elements do not comprise an exclusive list and a method or apparatus may contain additional blocks or elements.

Numerical descriptors such as 'first', 'second', and the like are used in this text simply as a way of differentiating between parts that otherwise have similar names. The numerical descriptors are not to be construed as indicating any particular order, such as an order of preference, manufacture, or occurrence in any particular structure.

Although the invention has been the described in conjunction with a certain type of apparatus and/or method, it should be understood that the invention is not limited to any certain type of apparatus and/or method. While the present inventions have been described in connection with a number of examples, embodiments and implementations, the present inventions are not so limited, but rather cover various modifications, and equivalent arrangements, which fall within the purview of the claims. Although various examples have been described above with a certain degree of particularity, or with reference to one or more individual embodiments, those skilled in the art could make numerous alterations to the disclosed examples without departing from the scope of this specification.

REFERENCES

[1] A. Michud et al., "Ioncell-F: ionic liquid-based cellulosic textile fibers as an alternative to viscose and Lyocell," *Text. Res. J.*, vol. 86, no. 5, pp. 543-552, 2016.

[2] T. Kakko, A. W. T. King, and I. Kilpelainen, "Homogenous esterification of cellulose pulp in [DBNH] [OAc]," *Cellulose*, vol. 24, no. 12, pp. 5341-5354, 2017.

[3] A. Parviainen et al., "Sustainability of cellulose dissolution and regeneration in 1,5-diazabicyclo[4.3.0]non-5-enium acetate: A batch simulation of the IONCELL-F process," *RSC Adv.*, vol. 5, no. 85, pp. 69728-69737, 2015.

[4] J. Canongia Lopes and L. P. Rebelo, "Ionic liquids and reactive azeotropes: the continuity of the aprotic and protic classes," *Phys. Chem. Chem. Phys.*, vol. 12, no. 8, pp. 1648-1648, 2010.

[5] W. Ahmad et al., "Feasibility of thermal separation in recycling of the distillable ionic liquid [DBNH] [OAc] in cellulose fiber production," *Chem. Eng. Res. Des.*, vol. 114, pp. 287-298, 2016.

[6] L. S. Sciarini, A. Rolland-Sabaé, S. Guilois, P. Decaen, E. Leroy, and P. Le Bail, "Understanding the destructuration of starch in waterionic liquid mixtures," *Green Chem.*, vol. 17, no. 1, pp. 291-299, 2015.

[7] Y. Kohno and H. Ohno, "Ionic liquid/water mixtures: From hostility to conciliation," *Chem. Commun.*, vol. 48, no. 57, pp. 7119-7130, 2012.

[8] A. M. Stepan, A. Monshizadeh, M. Hummel, A. Roselli, and H. Sixta, "Cellulose fractionation with IONCELL-P," *Carbohydr. Polym.*, vol. 150, pp. 99-106, 2016.

[9] A. M. Stepan, A. Michud, S. Hellstén, M. Hummel, and H. Sixta, "IONCELL-P&F: Pulp Fractionation and Fiber Spinning with Ionic Liquids," *Ind. Eng. Chem. Res.*, vol. 55, no. 29, pp. 8225-8233, 2016.

[10] K. Wippermann, J. Giffin, and C. Korte, "In Situ Determination of the Water Content of Ionic Liquids," *J. Electrochem. Soc.*, vol. 165, no. 5, pp. H263-H270, 2018.

[11] A. Garcia-Mendoza and J. C. Aguilar, "Analysis of water in room temperature ionic liquids by linear sweep, differential pulse and square wave cathodic stripping voltammetries," *Electrochim. Acta*, vol. 182, pp. 238-246, 2015.

[12] J. Viell and W. Marquardt, "Concentration measurements in ionic liquid-water mixtures by mid-infrared spectroscopy and indirect hard modeling," *Appl. Spectrosc.*, vol. 66, no. 2, pp. 208-217, 2012.

[13] C. D. TRAN, H. L. D. P. SILVIA, and D. OLIVEIRA, "Absorption of Water by Room-Temperature Ionic Liquids: Effect of Anions on Concentration and State of Water," *Appl. Spectrosc.*, vol. 57, no. 2, pp. 152-157, 2015.

[14] M. J. PELLETIER, "Quantitative Analysis Using Raman Spectrometry," *Appl. Spectrosc.*, vol. 57, no. 1, p. 20A-42A, 2003.

[15] O. Svensson, M. Josefson, and F. W. Langkilde, "Reaction monitoring using Raman spectroscopy and chemometrics," *Chemom. Intell. Lab. Syst.*, vol. 49, no. 1, pp. 49-66, 1999.

[16] R. W. Berg, Raman spectroscopy and ab-initio model calculations on ionic liquids, vol. 138, no. 11. 2007.

[17] V. H. Paschoal, L. F. O. Faria, and M. C. C. Ribeiro, "Vibrational Spectroscopy of Ionic Liquids," *Chem. Rev.*, vol. 117, no. 10, pp. 7053-7112, 2017.

[18] S. SATYEN, T. HIROI, K. IWATA, and H. HAMAGUCHI, "Raman Spectroscopy and the Heterogeneous Liquid Structure in Ionic Liquids," in Ionic Liquids Completely UnCOILed: *Critical Expert Overviews*, N. V. Plechkova and K. R. Seddon, Eds. 2015, pp. 165-187.

[19] P. Geladi, "Chemometrics in spectroscopy. Part 1. Classical chemometrics," *Spectrochim. Acta—Part B At. Spectrosc.*, vol. 58, no. 5, pp. 767-782, 2003.

[20] P. Geladi, B. Sethson, J. Nyström, T. Lillhonga, T. Lestander, and J. Burger, "Chemometrics in spectroscopy: Part 2. Examples," *Spectrochim. Acta—Part B At. Spectrosc.*, vol. 59, no. 9, pp. 1347-1357, 2004.

[21] P. Geladi and B. R. Kowalski, "Partial least-squares regression: a tutorial," *Anal. Chim. Acta*, vol. 185, no. C, pp. 1-17, 1986.

[22]M. Shen, Y. Zhang, K. Chen, S. Che, J. Yao, and H. Li, "Ionicity of Protic Ionic Liquid: Quantitative Measurement by Spectroscopic Methods," *J. Phys. Chem. B*, vol. 121, no. 6, pp. 1372-1376, 2017.

[23] T. Nakabayashi, K. Kosugi, and N. Nishi, "Liquid structure of acetic acid studied by Raman spectroscopy and Ab initio molecular orbital calculations," *J. Phys. Chem. A*, vol. 103, no. 43, pp. 8595-8603, 1999.

[24] E. Smith and G. Dent, *Modern Raman Spectroscopy—A Practical Approach*. Chichester, U K: John Wiley & Sons, Ltd, 2004.

[25] P. Larkin, Infrared and Raman spectroscopy: principles and spectral interpretation. 2011.

[26] Q. Sun, "The Raman O H stretching bands of liquid water," Vib. Spectrosc., vol. 51, no. 2, pp. 213-217, 2009.

[27] S. Cha et al., "Structures of ionic liquid-water mixtures investigated by I R and NMR spectroscopy," *Phys. Chem. Chem. Phys.*, vol. 16, no. 20, pp. 9591-9601, 2014.

Andersen C M, Bro R (2010) Variable selection in regression—a tutorial. J Chemom 24:728-737. https://doi.org/10.1002/cem.1360

Brereton R G (2003) Chemometrics: Data Analysis for the Laboratory and Chemical Plant. John Wiley & Sons, Ltd Cooper J B (1999) Chemometric analysis of Raman spectroscopic data for process control applications. Chemom Intell Lab Syst 46:231-247. https://doi.org/10.1016/S0169-7439(98)00174-9

Geladi P (2003) Chemometrics in spectroscopy. Part 1. Classical chemometrics. Spectrochim Acta—Part B At Spectrosc 58:767-782. https://doi.org/10.1016/S0584-8547(03)00037-5

Geladi P, Kowalski B R (1986) Partial leastsquares regression: a tutorial. Anal Chim Acta 185:1-17. https://doi.org/10.1016/0003-2670(86)80028-9

Geladi P, Sethson B, Nyström J, et al (2004) Chemometrics in spectroscopy: Part 2. Examples. Spectrochim Acta—Part B At Spectrosc 59:1347-1357. https://doi.org/10.1016/j.sab.2004.06.009

Gofurov S, Makhmanov U, Kokhkharov A, Ismailova O B (2019) Structural and Optical Characteristics of Aqueous Solutions of Acetic Acid. Appl Spectrosc 73:503-510. https://doi.org/10.1177/0003702819831325

Guizani C, Hellstén S, Witos J, Sixta H (2020) Quantitative Raman spectroscopy for the Ioncell™ process. Part 1: comparison of univariate and multivariate calibration methods for the quantification of water and protic ionic liquid components. Cellulose 27:157-170. https://doi.org/10.1007/s10570-019-02809-y Hyde A M, Calabria R, Arvary R, et al (2019) Investigating the Underappreciated Hydrolytic Instability of 1,8-Diazabicyclo[5.4.0]undec-7-ene and Related Unsaturated Nitrogenous Bases. Org Process Res Dev 23:1860-1871. https://doi.org/10.1021/acs.oprd.9b00187

Kaneko K, Yoshimura Y, Shimizu A (2018) Water concentration dependence of the refractive index of various ionic liquid-water mixtures. J Mol Liq 250:283-286. https://doi.org/10.1016/j.molliq.2017.12.009

Kauffmann T, Fontana M (2015) Simultaneous quantification of ionic solutions by Raman spectrometry and chemometric analysis. IMEKO XXI World Congr Kueppers S, Haider M (2003) Process analytical chemistry-future trends in industry. Anal Bioanal Chem 376:313-315. https://doi.org/10.1007/s00216-003-1907-0

Larkin P (2011) Infrared and Raman spectroscopy: principles and spectral interpretation Liu W, Cheng L, Zhang Y, et al (2008) The physical properties of aqueous solution of room-temperature ionic liquids based on imidazolium: Database and evaluation. J Mol Liq 140:68-72. https://doi.org/10.1016/j.molliq.2008.01.008

Nakabayashi T, Kosugi K, Nishi N (1999) Liquid structure of acetic acid studied by Raman spectroscopy and Ab initio molecular orbital calculations. J Phys Chem A 103:8595-8603. https://doi.org/10.1021/jp991501d Pavlović M, Baranovid G, Lovrekovic D (1991) Raman study of the bending band of water. Spectrochim Acta Part A Mol Spectrosc 47:897-906. https://doi.org/10.1016/0584-8539(91)80277-P Pelletier M J (2003) Quantitative analysis using Raman spectrometry. Appl Spectrosc 57:20A-42A Smith E, Dent G (2004) Modern Raman spectroscopy—a practical approach. John Wiley & Sons, Ltd, Chichester, U K Sun Q (2009) The Raman O H stretching bands of liquid water. Vib Spectrosc 51:213-217. https://doi.org/10.1016/j.vibspec.2009.05.002

The invention claimed is:

1. A method comprising:

a process of producing Lyocell-type man-made cellulosic fibers based on cellulose pulp dissolution in an ionic liquid (IL), dry-jet wet spinning of a solution in a water ($H_2O$) bath and a subsequent solvent recovery step, in which the IL and $H_2O$ are separated;

monitoring and/or controlling the process by quantification of water and/or one or more ionic liquid components in an ionic liquid (IL)/water ($H_2O$) mixture by:

obtaining one or more Raman spectra for the IL/H2O mixture; and using a quantitative calibration model with the one or more Raman spectra to quantify water and/or one or more ionic liquid components in the IL/H2O mixture; and simultaneously determining an acid, base and $H_2O$ content and/or $H_2O$ concentration and A:B ratio in the IL/$H_2O$ mixture.

2. The method according to claim 1, wherein the ionic liquid is a protic ionic liquid.

3. The method according to claim 2, wherein the ionic liquid is or comprises:

a non-imidazolium based protic ionic liquid.

4. The method according to claim 3, wherein using a quantitative calibration model involves univariate calibration, which is based on finding a relationship between a single spectral variable, peak intensity, peak area and/or peak shift, and an analyte concentration.

5. The method according to claim 4, comprising:

determining $H_2O$ concentration in the IL/$H_2O$ mixture utilizing a linear relationship between $H_2O$ peak area and an $H_2O$ mass fraction in the IL/$H_2O$ mixture.

6. The method according to claim 5, comprising:

determining a base concentration in the IL/$H_2O$ mixture utilizing a non-linear relationship between peak intensities and the base concentration.

7. The method according to claim 6, wherein the non-linear relationship is described with a power law model.

8. The method according to claim 6, wherein using a quantitative calibration model involves:

using multivariate calibration.

9. The method according to claim 8, wherein the multivariate calibration utilizes partial least squares (PLS) regression.

10. The method according to claim 1, comprising:

quantifying one or more ionic liquid degradation products.

11. The method according to claim 10, wherein the quantifying of one or more ionic liquid degradation products involves:

utilizing partial least squares (PLS) regression.

12. The method according to claim 11, wherein the quantifying of one or more ionic liquid degradation products involves:

dividing the one or more Raman spectra into two or more subintervals.

13. The method according to claim 1, comprising:

quantitative monitoring of an A:B ratio and/or $H_2O$ content for process control.

14. The method according to claim 1, comprising:

solvent purification based on a quantification of one or more ionic liquid degradation products.

15. The method according to claim 1, wherein the ionic liquid is or comprises:

a non-imidazolium based protic ionic liquid.

16. The method according to claim 1, wherein using a quantitative calibration model involves univariate calibration, which is based on finding a relationship between a single spectral variable, peak intensity, peak area and/or peak shift, and an analyte concentration.

17. The method according to claim 1, wherein using a quantitative calibration model involves:

using multivariate calibration.

* * * * *